(12) United States Patent
Horvath et al.

(10) Patent No.: US 11,690,973 B2
(45) Date of Patent: * Jul. 4, 2023

(54) SPLIT AND SIDE-PORTED CATHETER DEVICES

(71) Applicant: Becton, Dickinson and Company, Franklin Lakes, NJ (US)

(72) Inventors: Joshua Horvath, San Ramon, CA (US); Victor Politis, Framingham, MA (US); Stephen Richards, Holdrege, NE (US); Ronald Pettis, Cary, NC (US); Gary Searle, Norfolk, MA (US); Monica Rixman Swinney, Medford, MA (US); Natasha Bolick, Raleigh, NC (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/370,714

(22) PCT Filed: Jan. 4, 2013

(86) PCT No.: PCT/US2013/020342
§ 371 (c)(1),
(2) Date: Jul. 3, 2014

(87) PCT Pub. No.: WO2013/103864
PCT Pub. Date: Jul. 11, 2013

(65) Prior Publication Data
US 2015/0051583 A1    Feb. 19, 2015

Related U.S. Application Data

(60) Provisional application No. 61/583,564, filed on Jan. 5, 2012.

(51) Int. Cl.
*A61M 25/00*    (2006.01)
*A61M 5/142*    (2006.01)
(Continued)

(52) U.S. Cl.
CPC .... *A61M 25/0015* (2013.01); *A61M 5/14248* (2013.01); *A61M 5/158* (2013.01);
(Continued)

(58) Field of Classification Search
CPC ............ A61M 25/0015; A61M 25/007; A61M 25/0071; A61M 2025/0057;
(Continued)

(56) References Cited

U.S. PATENT DOCUMENTS 4,299,219 A   11/1981  Norris, Jr.
4,722,725 A    2/1988  Sawyer et al.
(Continued)

FOREIGN PATENT DOCUMENTS

CA    2051450         3/1992
CA    2179635 A1      7/1995
(Continued)

*Primary Examiner* — James D Ponton
(74) *Attorney, Agent, or Firm* — Dickinson Wright PLLC

(57) ABSTRACT

A catheter for use in medical applications is disclosed. The catheter comprises tubing with a tip hole at one end and an end portion at the other end. Fluid exits the catheter at the tip hole thereof. One or more alternative fluid pathway(s) are provided on the sidewall of the catheter to permit outflow of fluid medication from the catheter to ensure proper delivery of the medication to the intended target area, particularly when the tip opening is occluded or restricted for any reason.

24 Claims, 17 Drawing Sheets

(51) Int. Cl.
*A61M 5/158* (2006.01)
*A61M 5/168* (2006.01)

(52) U.S. Cl.
CPC ...... *A61M 5/16804* (2013.01); *A61M 25/007* (2013.01); *A61M 2005/16863* (2013.01); *A61M 2205/0216* (2013.01)

(58) Field of Classification Search
CPC .... A61M 2025/0188; A61M 2039/082; A61M 5/3291
See application file for complete search history.

(56) References Cited

U.S. PATENT DOCUMENTS

| | | | |
|---|---|---|---|
| 4,737,152 A | 4/1988 | Alchas | |
| 4,801,297 A * | 1/1989 | Mueller | A61M 25/0045 604/247 |
| 4,995,865 A | 2/1991 | Gahara et al. | |
| 5,069,673 A * | 12/1991 | Shwab | A61M 25/0023 604/526 |
| 5,267,979 A * | 12/1993 | Appling | A61B 17/22 137/537 |
| 5,425,723 A | 6/1995 | Wang | |
| 5,522,806 A | 6/1996 | Schönbächler | |
| 5,522,807 A | 6/1996 | Luther | |
| 5,545,143 A | 8/1996 | Fischell | |
| 5,664,567 A | 9/1997 | Linder | |
| 5,797,882 A | 8/1998 | Purdy et al. | |
| 6,017,328 A | 1/2000 | Fischell et al. | |
| 6,042,576 A * | 3/2000 | DeVries | A61M 25/007 604/264 |
| 6,261,272 B1 | 7/2001 | Gross et al. | |
| 6,346,095 B1 | 2/2002 | Gross et al. | |
| 6,517,521 B1 | 2/2003 | Ly | |
| 6,524,300 B2 * | 2/2003 | Meglin | A61M 25/007 604/246 |
| 6,533,763 B1 | 3/2003 | Schneiter | |
| 8,267,891 B2 * | 9/2012 | Dimalanta | A61F 9/00736 604/118 |
| 11,458,281 B2 * | 10/2022 | Horvath | A61M 25/0015 |
| 2002/0072720 A1 | 6/2002 | Hague et al. | |
| 2002/0095138 A1 * | 7/2002 | Lynch | A61M 5/14244 604/93.01 |
| 2003/0093029 A1 | 5/2003 | McGuckin, Jr. | |
| 2005/0107743 A1 | 5/2005 | Fangrow, Jr. | |
| 2007/0129691 A1 | 6/2007 | Sage, Jr. et al. | |
| 2008/0021375 A1 * | 1/2008 | Burns | A61M 39/0247 604/27 |
| 2008/0039796 A1 | 2/2008 | Nakajima | |
| 2008/0172012 A1 * | 7/2008 | Hiniduma-Lokuge | B21G 1/08 604/272 |
| 2008/0183128 A1 * | 7/2008 | Morriss | A61M 3/0283 604/35 |
| 2008/0243085 A1 * | 10/2008 | DeStefano | A61M 5/158 604/180 |
| 2008/0255447 A1 * | 10/2008 | Bourang | A61M 31/005 600/434 |
| 2008/0281290 A1 | 11/2008 | Yodfat et al. | |
| 2009/0062767 A1 | 3/2009 | Van Antwerp | |
| 2010/0022956 A1 | 1/2010 | Tipsmark et al. | |
| 2010/0160851 A1 * | 6/2010 | Dimalanta | A61M 1/008 604/22 |
| 2010/0228230 A1 | 9/2010 | Gately | |
| 2011/0112508 A1 | 5/2011 | Panzirer | |
| 2011/0313357 A1 | 12/2011 | Skutnik et al. | |
| 2013/0245555 A1 * | 9/2013 | Dirac | A61M 5/158 604/151 |
| 2014/0074028 A1 * | 3/2014 | Sonderegger | A61M 5/158 604/151 |

FOREIGN PATENT DOCUMENTS

| | | |
|---|---|---|
| CA | 2443769 | 10/2002 |
| EP | 2168625 A1 | 3/2010 |
| EP | 2289590 A1 | 2/2011 |
| JP | S62-112568 | 5/1987 |
| JP | H08-038619 A | 2/1996 |
| JP | 2005537893 | 12/2005 |
| JP | 2010-051700 A | 3/2010 |
| JP | 2010125229 A | 6/2010 |
| WO | WO-2010080715 A1 | 7/2010 |

* cited by examiner

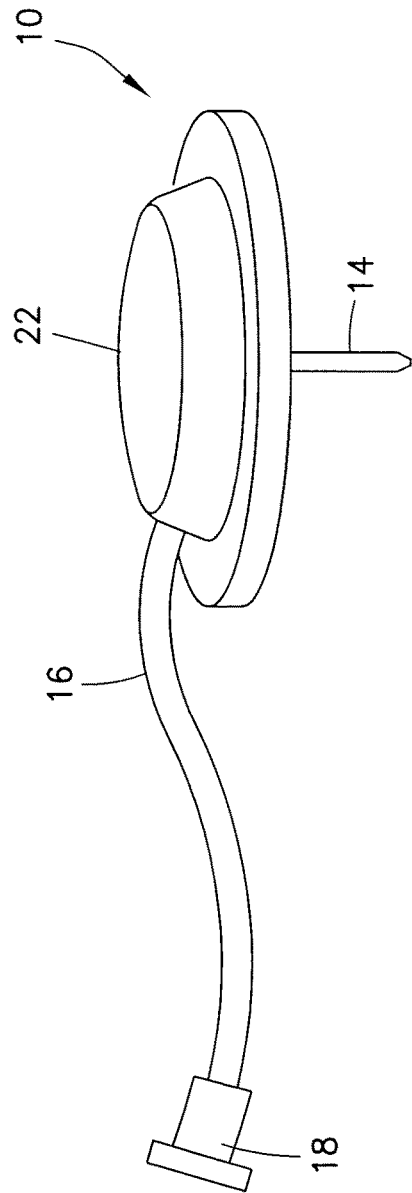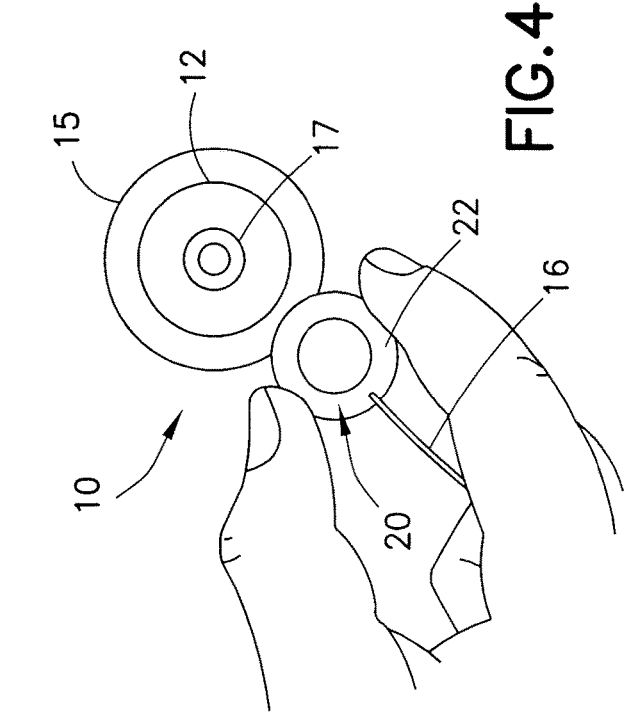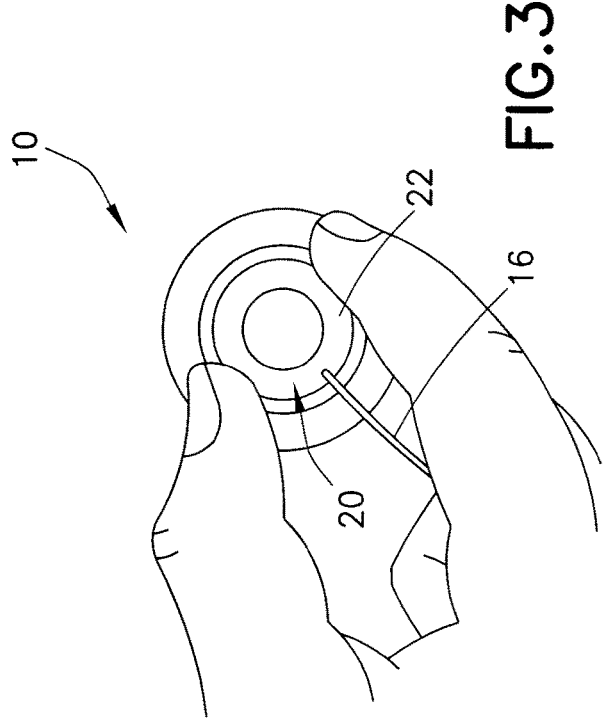

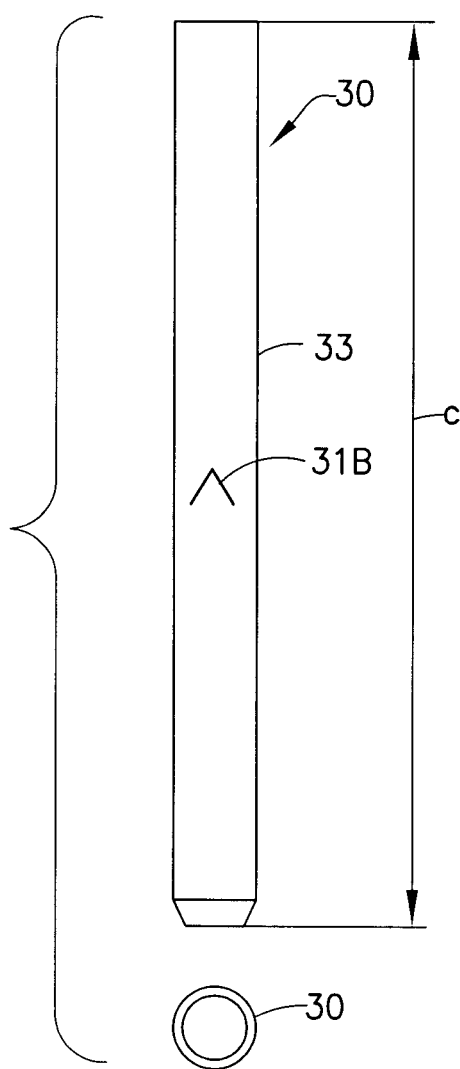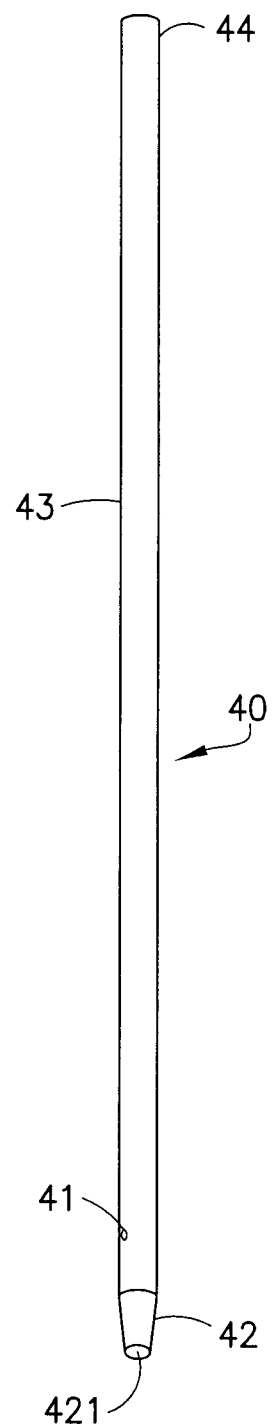
FIG.11
FIG.12

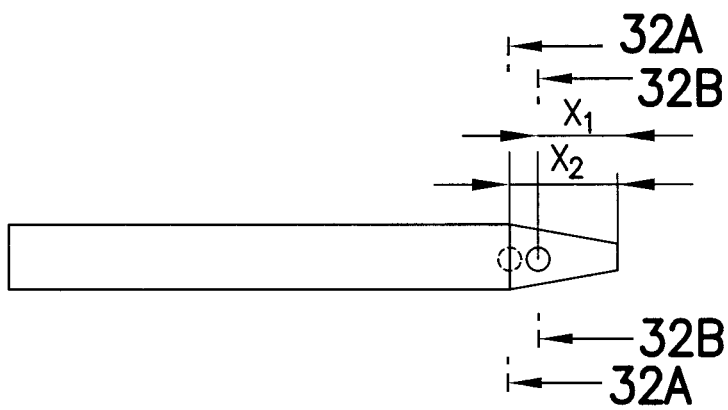
FIG.32A
FIG.32B
FIG.32
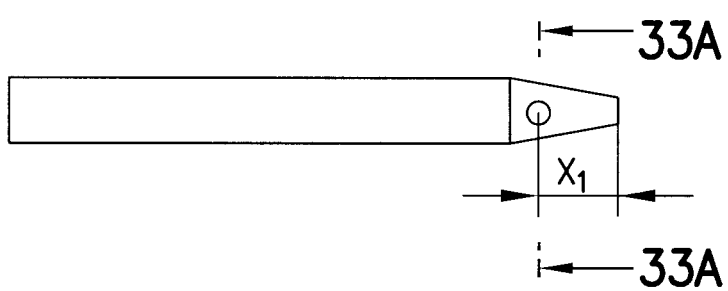
FIG.33A
FIG.33
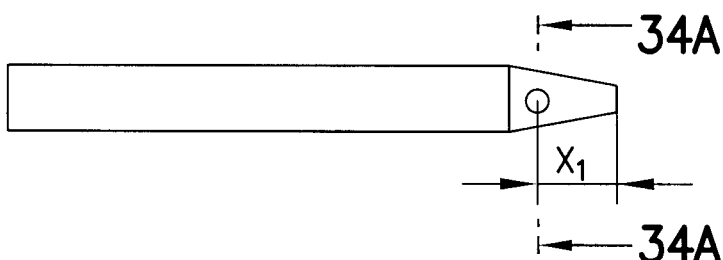
FIG.34A
FIG.34
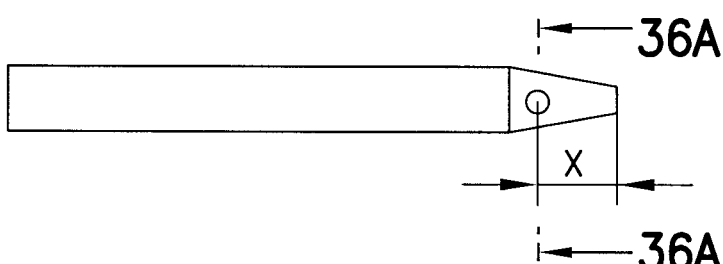
FIG.36A
FIG.36

SPLIT AND SIDE-PORTED CATHETER DEVICES

CROSS-REFERENCE TO RELATED APPLICATION

This application claims priority under 35 USC § 119(e) from U.S. Provisional Patent Application Ser. No. 61/583,564, filed on Jan. 5, 2012, the disclosure of which is incorporated herein by reference in its entirety.

FIELD OF THE INVENTION

The present invention relates generally to catheters used in medical treatment and methods of manufacture thereof.

BACKGROUND OF THE INVENTION

A conventional peripheral or intravenous catheter assembly 1 is illustrated in FIG. 1 in cross-section. The assembly 1 includes a wedge 3, usually made of a hard substance such as metal or a rigid plastic and having a funnel shape, to which an end portion 6 of the catheter tubing 4 is frictionally attached to connect the catheter tubing 4 to the wedge 3 and a catheter hub or adapter 2. The wedge 3, to which the catheter tubing 4 has been attached, is secured to the hub or adapter 2 to form the catheter assembly 1. Fluid exits the tip 5 of the catheter tubing 4. Although the type of catheter assembly illustrated in FIG. 1 is for a conventional intravenous catheter assembly, the manner of attachment of the catheter can be similar in non-intravenous catheter assemblies, for example, for use in a subcutaneous infusion set. That is, in a subcutaneous infusion set, a catheter and a wedge can be secured to a base to form a catheter assembly.

FIGS. 2-4 illustrate a conventional infusion set 10 that is used to deliver insulin to a diabetic patient from an insulin pump (not shown). As illustrated in FIG. 2, the infusion set 10 includes a hub or fluid connector 22 that detachably connects with a base 12 (see FIG. 4), a fluid tubing set 16 and a connector 18 that attaches to a pump. FIGS. 3 and 4 illustrate the conventional infusion set 10 in which the line set 20, which includes the hub 22 and the fluid tubing set 16, is attached to or detached from the base 12. The base 12 includes an infusion adapter 17 for connecting with the fluid connector or hub 22. An adhesive pad 15 is attached to the base 12 to secure the base to a user's skin. The catheter 14 is attached to the base 12, for example, with a wedge (not shown). The catheter 14 is similar in shape to that which is more clearly illustrated in FIG. 1. It is noted, however, that catheters for infusion sets (for example, subcutaneous or intradermal) target layers of the skin, and are generally shorter than intravenous catheters.

One type of conventional infusion set is sold as the Quick-Set® infusion set by Medtronic. In such devices, the infusion set includes a catheter assembly connected to a pump (e.g. MiniMed Paradigm® insulin pump by Medtronic) via a tubing set, and a separate insertion device inserts and/or attaches the catheter assembly to a user via an introducer needle provided as a part of the infusion set. The catheter assembly can also be inserted manually into a user's skin. The infusion set and insertion device can also be combined, as in the Mio® infusion set sold by Medtronic, which is an "all-in-one" design that combines the infusion set and insertion device into one unit.

Another type of insulin infusion device known as a "patch pump" has also become available. Unlike a conventional infusion pump, a patch pump is an integrated device that combines most or all of the fluid components in a single housing that is adhesively attached to an infusion site, and does not require the use of a separate infusion (tubing) set. A patch pump adheres to the skin, contains insulin (or other medication), and delivers the drug over a period of time, either transdermally, or via an integrated subcutaneous catheter. Some patch pumps communicate with a separate controller device wirelessly (such as one sold under the brand name OmniPod®), while others are completely self-contained. Both conventional pump infusion sets and patch pumps need to be reapplied on a frequent basis, such as every three days, as complications may otherwise occur.

In all such devices that have flexible catheters, the flexible catheter is inserted into the skin by means of an introducer needle, as is well known in the art. Once the introducer needle is removed, generally through the catheter, the catheter is enabled to deliver insulin. But, when the catheter is attached to a user, the catheter can become occluded. In other words, the tip of the catheter, from which insulin flows out to the user, becomes obstructed due to the formation of a blockage, such as tissue inflammation. In addition, the catheter may develop kinking, such that the catheter becomes snagged, knotted, or sharply bent to form a kink that impedes or blocks fluid flow out of the tip of the catheter.

Kinking is considered to be the cessation of flow through the catheter, due to mechanical causes, such as sliding back (accordion or bellows) or folding back on the introducer needle during insertion. This failure mode could be the result of insufficient interference between the inner diameter of the catheter and the outer diameter of the introducer needle. In addition, kinking may also occur during deployment from having a blunt end on the lead end of the catheter, which may cause excess force to be transmitted to the catheter as the catheter initially penetrates the outer surface of the skin. Similarly, excessive bounce or vibration in the insertion mechanization may also result in excessive force being transmitted to the catheter.

Occlusion is the cessation of flow due to biologic or pharmacologic causes and/or mechanical obstruction of the catheter tip by tissue structures, as described above, and these failures typically occur during the use cycle. Depending on the level of irritation caused by the catheter and the movement allowed by the catheter adapter/hub, the tissue can become inflamed as part of a foreign body response, resulting in reduced insulin uptake. Further, there is a tendency for insulin to crystallize when flow is reduced to a minimum (low basal flow) or temporarily stopped, e.g. for bathing, swimming or extended periods, during which time the infusion set is disconnected from the pump. Insulin crystallization that is allowed to proliferate will ultimately occlude the catheter to a point at which the required pump pressure can exceed the normal flow conditions of the pump and trigger an alarm.

The tip of the catheter can also be blocked without inflammation of surrounding tissue. For instance, the application of an external force to the infusion site, can cause the open end of the catheter to press against tissue structures in the body, resulting in an occlusion. This phenomenon has been demonstrated in model tests in which a slight force is applied to the infusion hub in a downward direction, and it can be observed, via fluoroscopy, that the catheter is occluded at the tip.

It is highly desirable, to minimize the risks of occlusion, kinking, and other complications such as tissue inflammation and foreign body response, while maintaining a degree of comfort to the user, because once the catheter becomes fully or partially blocked, infusion therapy cannot take place at all, or can be reduced below target flow rates.

Soft plastic catheters are prone to kink or occlude with normal wear, while the rigid catheters are often found to be uncomfortable to the user, because the rigid catheter tends to move around within the tissue of the user. Both soft plastic catheters and rigid catheters can also exhibit other undesired complications such as tissue inflammation and foreign body response.

Kinking of the catheter can also occur during the infusion or use cycle. A typical cause of this failure is the placement of the catheter into tissue which undergoes significant movement during physical activity. In addition, conditions that cause deformation of the catheter may contribute to kinking.

Insulin infusion devices currently available on the market generally incorporate either a flexible catheter (made of soft materials, such as soft plastic, fluorinated polymers, Teflon®, and so forth) or a rigid catheter, such as a stainless steel cannula.

A rigid cannula has a sharp tip, which is used to pierce the skin, similar to an introducer needle in a conventional inserter. Such products are recommended for individuals who have a high incidence of catheter kinking and are not recommended for use beyond two days, because they can occlude for the reasons mentioned above.

Accordingly, a need exists for an improved catheter design and construction that, in the event the catheter becomes occluded, allows infusion to continue to take place at the target area or tissue as well as reducing instances of kinking and/or occlusion.

SUMMARY OF THE INVENTION

Among the objects of the present invention are to provide catheters configured and arranged to optimize fluid flow out of the catheter while maintaining column strength for catheter insertion, axial and radial strength for resistance to deformation, flexibility for user comfort, and tensile strength for durability, insertion and removal.

These and other objects are substantially achieved by providing a catheter assembly wherein the catheter provides one or more exit paths in addition to the main exit for infusion at the tip of the catheter, and permits proper delivery of insulin doses to the user when a blockage, such as kinking and/or occlusion, occurs.

In one embodiment, the catheter may include an elongate member having a sidewall, first and second end portions, and an opening at each of the end portions, a primary fluid pathway through the elongate member between the openings of the end portions of the elongate member, and a secondary fluid pathway in fluid communication with the primary fluid pathway. The secondary fluid pathway includes one or more side ports in the sidewall of the elongate member. The side port(s) is/are configured to release, depending on their number, size and location on the elongate member, controlled amounts of infusate into the skin of a patient.

In another embodiment, the catheter may include an elongate member having a sidewall, first and second end portions, and an opening at each of the end portions, a primary fluid pathway through the elongate member between the openings of the end portions of the elongate member, and a secondary fluid pathway in fluid communication with the primary fluid pathway. The secondary fluid pathway includes a self-closing opening in the sidewall of the elongate member.

Another embodiment provides a method of administering infusate via a catheter. The method includes the steps of providing a catheter with an elongate member having a sidewall, first and second end portions, and an opening at each of the end portions, a primary fluid pathway through the elongate member between the openings of the end portions of the elongate member, and a secondary fluid pathway in fluid communication with the primary fluid pathway. The secondary fluid pathway includes one or more side ports in the sidewall of the elongate member. The side ports are configured to release controlled amounts of infusate, depending on their number, size and location on the elongate member, into the skin of a patient. The method further includes inserting the catheter into a patient and administering infusate to the patient via one or both the primary and secondary fluid pathways of the catheter.

Another embodiment also provides a method of administering infusate via a catheter. The method includes providing a catheter with an elongate member having a sidewall, first and second end portions, and an opening at each of the end portions, a primary fluid pathway through the elongate member between the openings of the end portions of the elongate member, and a secondary fluid pathway in fluid communication with the primary fluid pathway. The secondary fluid pathway includes a self-closing opening in the sidewall of the elongate member. The method includes inserting the catheter into a patient and administering infusate to the patient via one or both the primary and secondary fluid pathways of the catheter.

Another embodiment provides an infusion system having a base, a hub detachably attached to the base, and a pump. The system includes a fluid tubing set that connects the pump and the base and a catheter with a primary fluid pathway through an elongate member, a secondary fluid pathway at in fluid communication with the primary fluid pathway. The secondary fluid pathway includes one or both of a side port and a self-closing opening in a sidewall of the elongate member.

Additional and/or other aspects and advantages of the present invention will be set forth in the description that follows, or will be apparent from the description, or may be learned by practice of the invention.

BRIEF DESCRIPTION OF THE DRAWINGS

The various objects, advantages and novel features of the exemplary embodiments of the present invention will be more readily appreciated from the following detailed description when read in conjunction with the appended drawings, in which:

FIG. 2 is a perspective view of a conventional infusion set;

FIG. 3 is a top view of the infusion set of FIG. 2;

FIG. 4 is a top view of the conventional infusion set of FIG. 2 in which the line set is detached from the base;

FIGS. 9-11 illustrate various split catheter configurations in accordance with embodiments of the present invention;

FIG. 12 is a perspective view of a catheter that is provided with a single side port in accordance with an embodiment of the present invention;

FIG. 32 illustrates a front view of a side-ported catheter having two side ports on different planes, the port configurations having different distances between the side port and the tip;

FIG. 32A illustrates a cross-section taken along line 32A-32A of FIG. 32;

FIG. 32B illustrates a cross-section taken along line 32B-32B of FIG. 32;

FIG. 33 illustrates a front view of a side-ported catheter having a through hole that forms two side ports on a single plane;

FIG. 33A illustrates a cross section taken along lines 33A-33A of FIG. 33;

FIG. 34 illustrates a front view of a side-ported catheter having a single side port;

FIG. 34A illustrates a cross section taken along lines 34A-34A of FIG. 34;

FIG. 36 illustrates a front view of a side-ported catheter having a single side port in accordance with an embodiment of the present invention; and FIG. 36A illustrates a cross section taken along lines 36A-36A of FIG. 36.

DETAILED DESCRIPTION OF THE EXEMPLARY EMBODIMENTS

Figure 1:
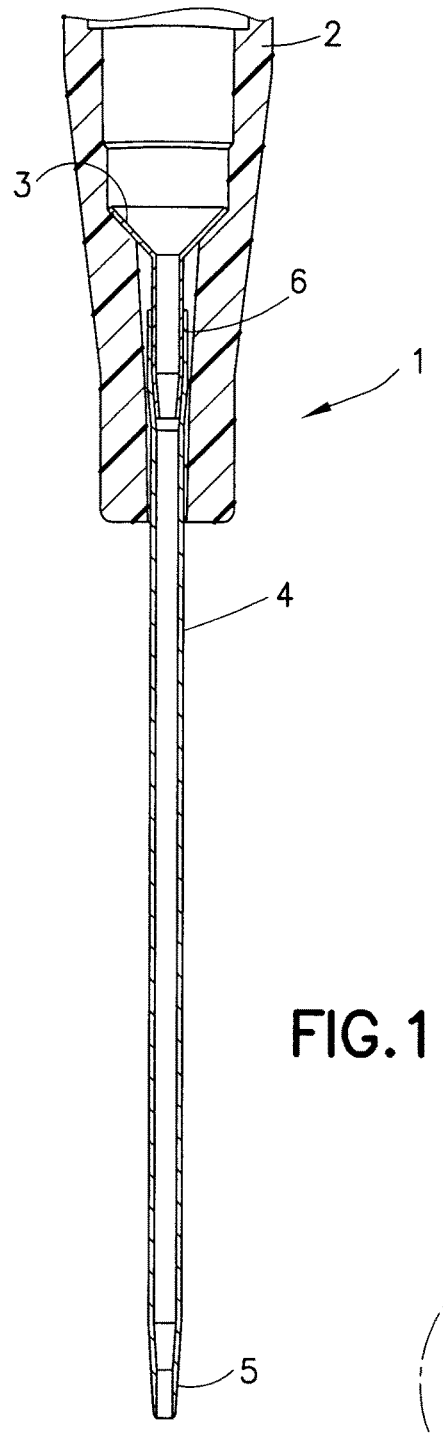
FIG. 1 is an enlarged cross-sectional view of an end portion of a conventional peripheral or intravenous catheter assembly.

Reference will now be made in detail to embodiments of the present invention, which are illustrated in the accompanying drawings, wherein like reference numerals refer to like elements throughout. The embodiments described herein exemplify, but do not limit, the present invention by referring to the drawings. As will be understood by one skilled in the art, terms such as up, down, bottom, and top are relative, and are employed to aid illustration, but are not limiting.

The exemplary embodiments described below provide improved catheters for use with infusion sets and/or patch pumps, or as intravenous or peripheral catheters. For example, in the event of catheter kinking, occlusion and other undesirable complications, such as tissue inflammation and foreign body response that may act to block or reduce the flow of medication fluids out of the catheter to the patient, an additional pathway or pathways permit the delivery of the medication at the intended target. Such exemplary embodiments are presented in separate descriptions, although the individual features of these embodiments can be combined in any number of ways to meet the therapeutic needs of the user.

The discussed catheter embodiments are generally flexible, and provide a high level of comfort to the user. The catheters can deliver insulin or other medicaments to the target tissue or area even if the main infusion area, usually at the tip of the catheter, becomes occluded.

Figure 5:
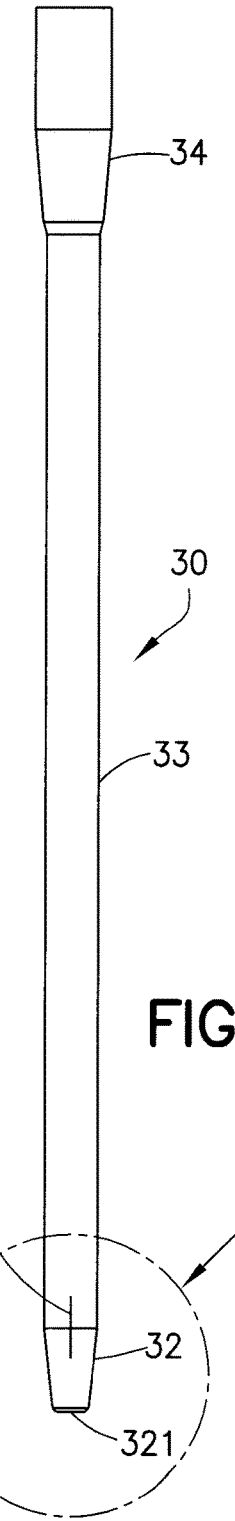
FIG. 5 is front view of a catheter that is provided with a split on a sidewall in accordance with an embodiment of the present invention.
Figure 6:
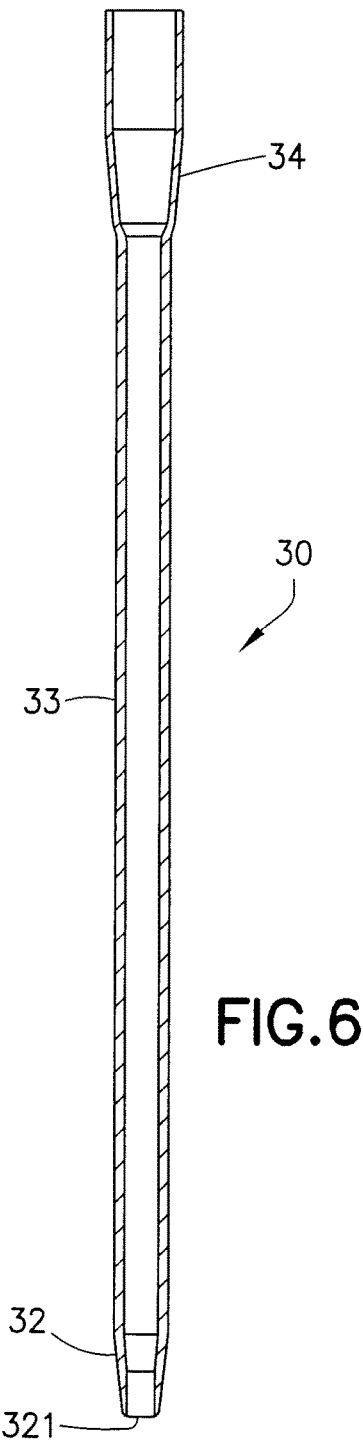
FIG. 6 is a cross-sectional view of the catheter of FIG. 5.
Figure 7:
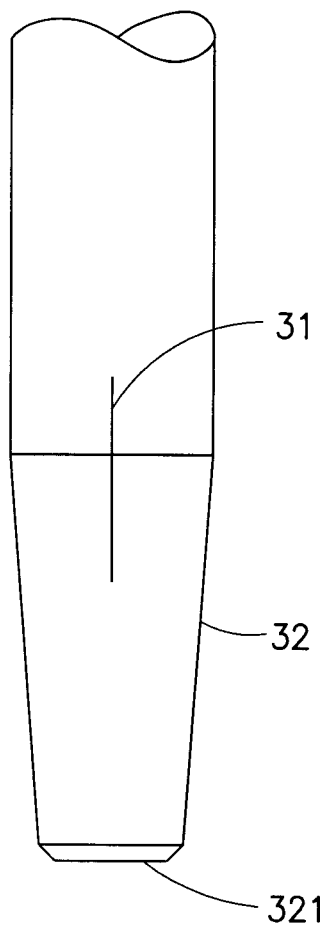
FIG. 7 is an enlarged view of the tip of the catheter of FIG. 5, with the split shown in a closed position.
Figure 8:
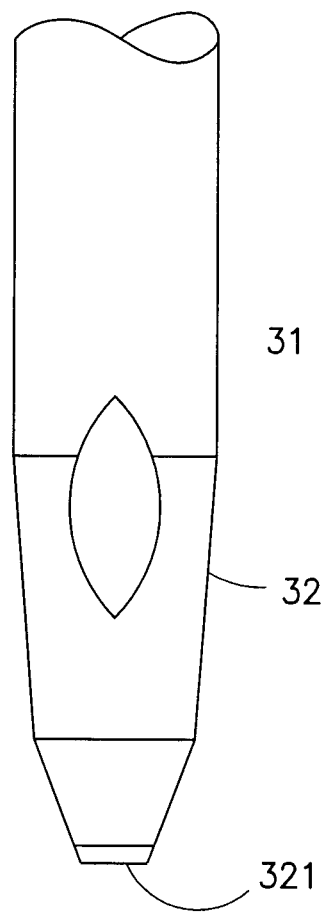
FIG. 8 is an enlarged view of the tip of the catheter of FIG. 5, with the split shown in an open position.

FIGS. 5 and 6 illustrate an embodiment of the present invention, in which a catheter 30 comprises a length of tubing 33, a tapered tip 32 at one end of the tubing 33 and an end portion 34 at the other end of the tubing 33, away from the tip 32. The tip 32 includes a tip hole 321. The catheter 30 includes a cut or split 31 penetrating through its side wall that is shown to be located at a general location where the tubing 33 meets the tip 32. Alternatively, the split 31 can be located anywhere on the catheter 30 that will ultimately be deployed in the target tissue. FIG. 6 is a cross-sectional view of the catheter 30. FIGS. 7 and 8 are enlarged views of the distal end of the catheter 30 to better illustrate the split 31. FIG. 7 illustrates the split 31 in a closed state and FIG. 8 illustrates the split 31 in an opened state. In the open state, the split 31 communicates with the internal lumen of the catheter 30.

Other than the tapered tip 32, the tubing 33 has a substantially constant cross-sectional area prior to installation of the tubing 33 onto a wedge. Such installation onto a wedge, whether for an intravenous catheter hub or for a catheter assembly on an infusion set, forms the end portion 34 illustrated in FIGS. 5 and 6. Although the end portion 34 is illustrated as being deformed by a wedge, the wedge itself is omitted from FIGS. 5 and 6 for clarity. According to one embodiment, if the tubing 33 is removed from the wedge, the tubing will return to the previous shape of a tube with a substantially constant cross sectional area.

The primary infusion path is via the tip hole 321 and the secondary infusion path is via the split 31. This embodiment of the present invention allows for a secondary infusion path to open, if the primary infusion path becomes occluded or if the flow rate through the primary infusion path is insufficient.

The catheter 30 of this embodiment can be an integral part of an insulin infusion set, as illustrated in FIG. 2, and is modified to include one or more splits 31 that can be located proximal to the distal tip or tip hole 321 of the catheter 30, preferably at a distance of approximately 1.0 mm to 4.0 mm, depending on depth of the targeted tissue layer. According to one embodiment, the split 31 (or splits) has a single axis, which is preferably oriented along the length of the catheter 30. Two or more of the splits 31 can be crossed, such that two splits 31 can be oriented 90° from each other. Other variations for the splits are envisioned in which splits can be crossed at various angles, e.g. 30 degrees, 45 degrees, etc., and the lengths of the splits can be the same or different.

FIG. 6 illustrates a single split 31, but the number of splits on a catheter may be plural. A plurality of the splits 31 may also be spaced apart such that they are located 180° around the catheter 30 from each other, for instance, at the same distance from the distal tip or tip hole 321 of the catheter 30. In addition, the splits 31 can be staggered, for instance at different distances from the distal tip 321 of the catheter 30, and at the same or different circumferential locations on the catheter 30. Thus various configurations are envisioned in which one or more splits 31 are located anywhere on the catheter 30.

When the catheter 30 is part of an infusion set, the splits 31 may be positioned on the catheter 30 to be located within the target tissue, e.g. subcutaneous (SC), intradermal (ID) and/or intramuscular (IM), once the catheter 30 has been deployed. In other words, the positions of the splits 31 may be created to specifically target one or more layers of the target tissue.

As illustrated in FIGS. 7 and 8, the split 31 is configured to open when the internal pressure of the catheter 30 reaches a specific threshold due to the release of insulin into the catheter 30 by the infusion pump. For example, if the tip hole 321 is blocked, due to occlusion or kinking, thus restricting or preventing the release of insulin via the tip hole 321. But the split can open even if there is no occlusion in the tip hole 321.

When the internal pressure within the catheter 30 reaches a specific threshold (cracking pressure), the pressure causes the split 31 to open and form a secondary infusion pathway, as illustrated in FIG. 8. Preferably, the cracking pressure for opening the split 31 should be greater than the typical pressure that is encountered within the catheter 30 during insulin infusion, but lower than the pressure required to trip the high pressure alarm in the infusion pump (which indicates catheter blockage), such that the split 31 will open only if the tip hole 321 becomes occluded. Catheter occlusion may be due to one or more causes, including insulin crystallization, tissue irritation, tissue interference with the catheter tip opening, and kinking of the catheter.

The cracking pressure for opening the split 31 can be determined empirically, by varying the length of the split 31, while "dead-ending" or clamping the catheter tip 32 and increasing the internal pressure within the catheter 30.

When the cracking pressure for the split 31 has been reached, the split 31 will open, as illustrated in FIG. 8, thereby creating a secondary infusion path that opens after the primary infusion path at the distal tip or tip hole 321 has become occluded. It is noted that the catheter 30 can slightly deform from its closed shape, as illustrated in FIG. 7, to that illustrated in FIG. 8, when the split 31 is opened to form a secondary infusion pathway. FIG. 8 illustrates deformation of the catheter tip 32. In this instance, as the split 31 is opened, the tip 32 and tubing 33 deform slightly to accommodate the opening of the split 31, and it is possible that such deformation may help remove an existing occlusion formed at the tip hole 321.

There are additional advantages to this embodiment of the invention. In a catheter 30 with one or more splits 31, there is minimal loss of column strength and virtually no loss of tensile strength in the catheter 30.

In an embodiment in which there is a plurality of splits 31 in a catheter 30, a split near the tip hole 321 can be designed to preferentially provide infusion upon occlusion at the tip hole 321. But once the tip hole 321 occludes, infusion can be sequentially provided through the splits, according to increasing degrees of cracking pressure. In other words, with a plurality of splits 31 on the catheter 30, each of the splits 31 will have its own cracking pressure, which will preferably be different, such that only one split 31 is opened at that time. If for any reason, the split 31 having the lowest cracking pressure is prevented from opening, the split with the next highest cracking pressure will open, and so on. It is also envisioned, however, that a plurality of splits 31, each having the same cracking pressure, may be placed on the catheter, so that infusion is simultaneously provided to all of the splits at the same time.

Creating one or more splits 31 on a catheter 30 can be made simply and cost effectively. The splits 31 may be cut in the same manner as cuts are made in a split septum, for example, with a laser or knife edge. The splits may be of different lengths, but are generally small, in the range of about 0.079 inch (2.0 mm) or less, as illustrated in FIG. 3E. Such a process is quick, inexpensive, and can even be incorporated into the catheter molding process.

By creating secondary and/or additional infusion paths, a split catheter, as illustrated in FIG. 6, can function to increase the longevity of the infusion site by providing an alternate, unused infusion path that is activated only when the primary infusion path occludes or is shut down. The split catheter 30 can be incorporated into an infusion set, as is illustrated in FIG. 2, that dispenses insulin to a patient. Where there are a multiple number of splits 31 on a catheter 30, the splits can be configured to have increasing cracking pressures, so that the splits 31 can sequentially open if the internal pressure of the catheter 30 continues to increase. Such a situation can occur as each opening is sequentially occluded over time. This configuration can be made by varying the length of the splits 31 to correspond to different cracking pressures, for instance. Although the split 31 is shown as a single split in the wall of the catheter 30, there can be additional cuts or configurations (e.g. cross-cut to form a cross-spilt) so that the level of internal pressure at which the split 31 opens can be further controlled by such design.

Figure 9:
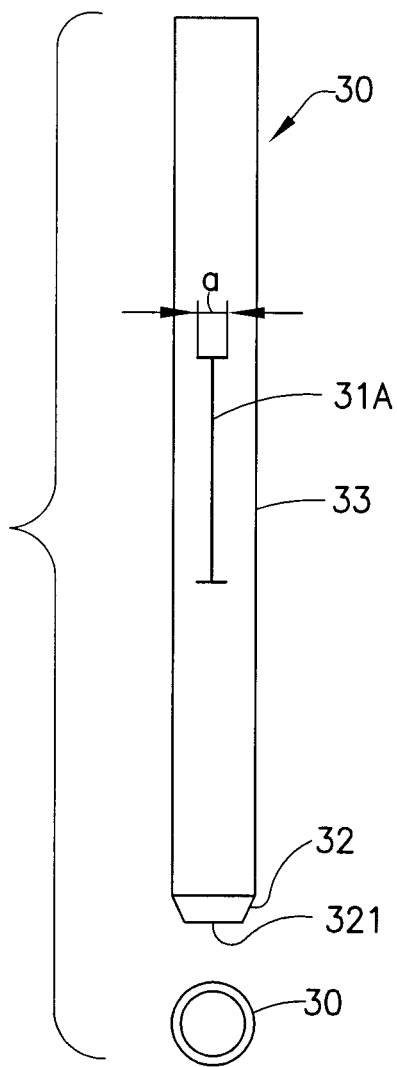
Figure 10:
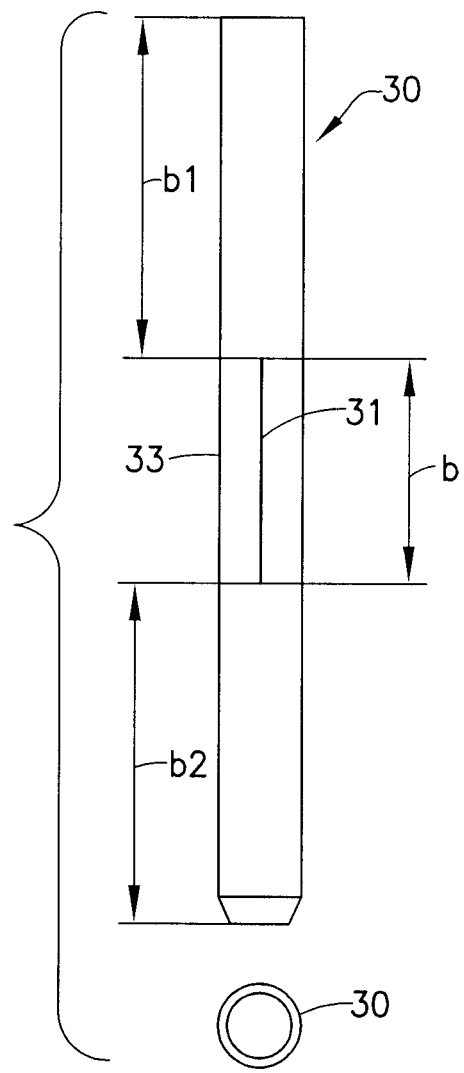

FIGS. 9-11 illustrate split catheters of varying split designs, along with their cross-sectional views. FIG. 9 illustrates a split catheter 30 having an "I"-shaped slot or split 31A with a longitudinal length of about 0.078 inch (2.0 mm) and lateral lengths of about 0.01 inch (0.25 mm). FIG. 10 illustrates a split catheter 30 having a straight slot or split 31 with a length of about 0.078 inch (2.0 mm). FIG. 11 illustrates a split catheter 30 having a flap configuration split 31B, the circumferential length of which extends approximately 60 degrees to 120 degrees of the circumference of the catheter 30.

The splits illustrated in FIGS. 9-11 are shown as being formed by straight line cuts, but they are not limited to such geometry. The splits may include curved split shapes, such as a "C"-shaped split, "S"-shaped split or "U"-shaped split (not shown). FIGS. 9-11 illustrate a cannula or catheter of approximately 24 gauge, having an outer diameter of approximately 0.027 inch (0.69 mm) and a wall thickness of about 0.004 inch (0.1 mm). The split catheters can be used with conventional insulin pump systems, such as the Animas One Touch Ping, which can provide a normal delivery speed in units (U) per second (s) of 0.5-0.9 U/s of insulin and a slow delivery speed of 0.2-0.4 U/s, where one (1) unit of U-100 insulin is 10 microliters.

The splits 31 can be positioned at different locations on the catheter 30, as previously described, and in addition one or more of such splits 31 can be substituted for various openings on the catheter, or used in combination thereof, as will be described in the following embodiments.

FIGS. 12-31 also illustrate various embodiments in which secondary or additional pathways are provided for insulin in addition to the tip hole of the catheter. The embodiments illustrated in FIGS. 12-31 include end portions, like the end portion 34 in FIGS. 5 and 6. But unlike end portion 34 of FIGS. 5 and 6, for clarity, the end portions in FIGS. 12-31 are shown without the deformation associated with installation on a wedge. These end portions, however, once installed on a wedge, would deform similar to the end portion 34 illustrated in FIGS. 5 and 6.

FIGS. 12-31 illustrate side-ported catheter embodiments. These embodiments are subcutaneous catheters that are perforated with one or more holes extending completely through a side wall of the tubing to form one or more side ports and provide an alternate flow path (i.e., other than the tip hole) during insulin infusion. Existing insulin infusion subcutaneous catheters allow medicament flow out of the tip of the catheter (tip hole). As described previously, the tip hole can become occluded by the surrounding tissue that can seal off the tip of the catheter during insertion or due to other factors. Catheters may also be subjected to kinking or bending during insertion, which may also limit insulin flow to the target tissue from the catheter.

When occlusion or kinking occurs to block flow of insulin out of the catheter tip (tip hole), catheters with one or more perforations, or side ports, allow secondary pathways that will remain open and redirect the flow of medicaments, such as insulin. Because of this, side-ported catheters with such secondary pathways ensure that correct dosing to the patient occurs. In the case of insulin dosing, unexplained high blood glucose levels and pump occlusion alarms are prevented. In addition, an infusion site may last longer, thus improving the comfort level to the patient who need not be subject to additional catheter insertions.

During the development of various perforated catheter embodiments, multiple perforated catheter designs were evaluated that differed in hole sizes, hole locations and catheter materials. These are all factors that were observed to affect catheter structural integrity, infusion site leakage, and insertion reliability. Preferably, to ensure the catheter port is contained within the subcutaneous space, the perforated hole 41 should not be closer than 2.5 mm from the surface of the skin (or the thickness of the intra-dermal space). Additionally, the side holes should be strategically placed in the catheter to ensure that enough material is provided around the side holes, to prevent collapse of the catheter. During testing of various embodiments of side-ported catheters, it was discovered that the total side port cross-sectional area should be similar to or less than the cross-sectional area at the catheter tip or the tip hole 421.

In addition to the perforated holes or side ports, other geometries, such as longitudinal splits or crosses (crossed-splits), as discussed above, may be substituted for the perforated holes or side ports, or may be used together with the perforated holes. Due to the one or more side-ported holes on the catheter that provide alternate path or paths, insulin or other fluid medicament coming out of the catheter can infuse into the patient with low resistance.

The side ports may be created in a manner similar to the earlier mentioned splits, i.e., via lasing or mechanical processes. Lasing is preferred in making the side ports due to their small diameters, but mechanical drilling can produce similar results. In general, lasing or mechanical drilling are preferred processes in forming the side ports, and such processes can be incorporated into the catheter molding process. An advantage of lasing the side ports is that the ports do not have to be round. In other words, elongated holes or ports with the same open area as a round port or hole may improve both the column strength and the tensile strength of the catheter.

Figure 13:
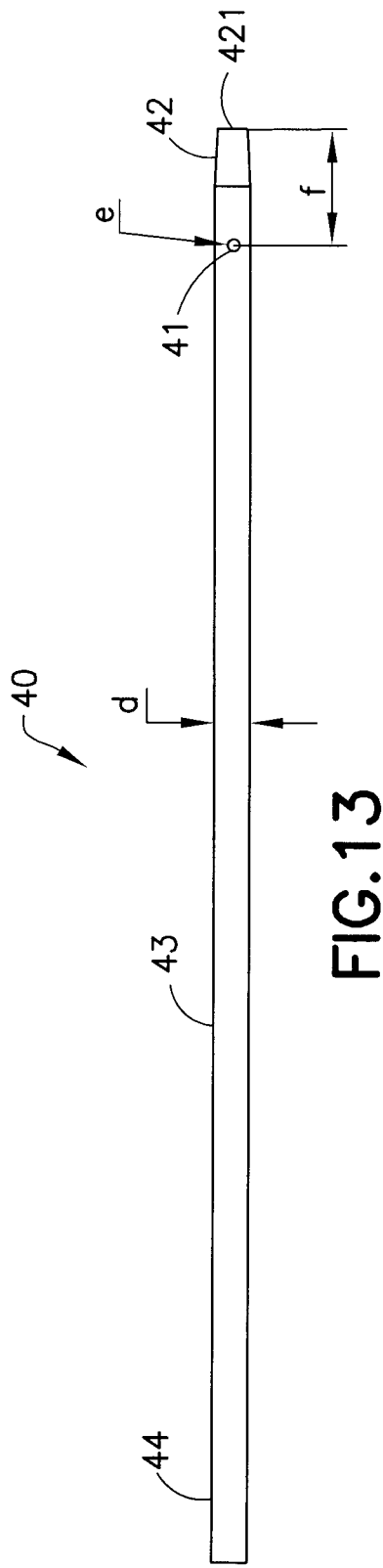
FIG. 13 is front view of the catheter of FIG. 12.
Figure 14:
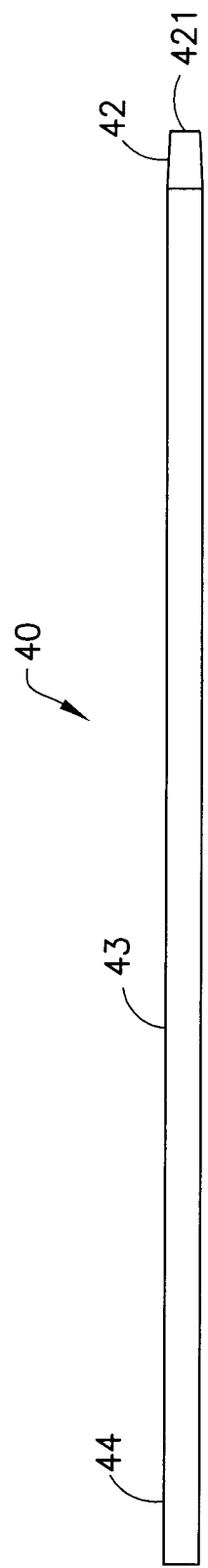
FIG. 14 is a side view of the catheter of FIG. 13.

FIG. 12 illustrates an embodiment of the present invention, in which a catheter 40 is provided with a single side port 41. The catheter 40 comprises a tubing 43, a tapered tip 42 having a tip hole 421, and an end portion 44 (simplified) opposite the tip 42. The location of the side port 41, as measured from the tip hole 421, can vary according to the thickness of the desired dermal layer so that infusion can be delivered to the target tissue layer. FIG. 13 is a front view of the catheter 40. In an exemplary embodiment, the distance "f" is approximately 2.0 mm±0.3 mm. FIG. 14 is a side view of the catheter 40. The outer diameter "d" of the catheter 40 is approximately 0.57 mm±0.04 mm. The diameter "e" of the side port 41 is approximately 0.15 mm±0.025 mm.

Figure 15:
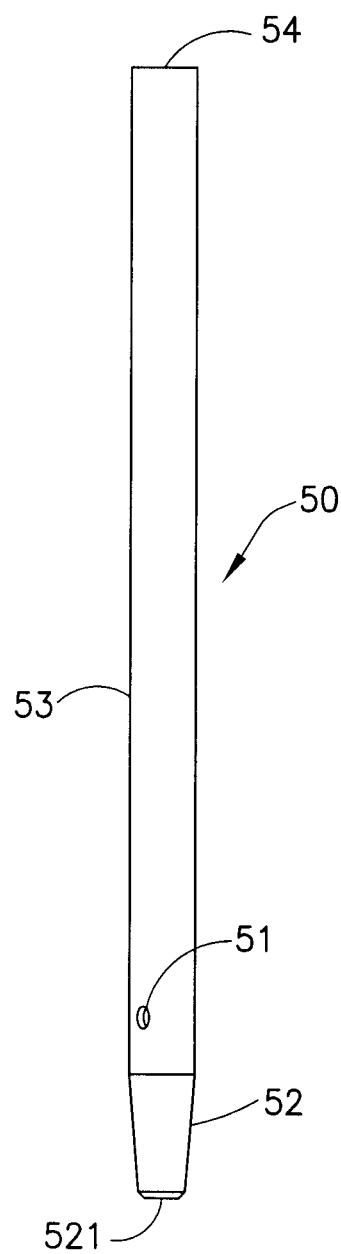
FIG. 15 is a perspective view of a catheter that is provided with three staggered side ports in accordance with an embodiment of the present invention.
Figure 16:
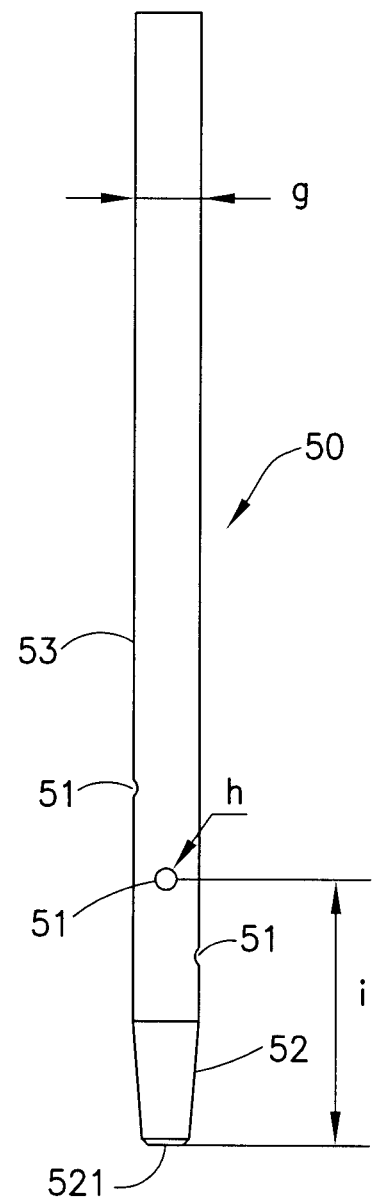
FIG. 16 is front view of the catheter of FIG. 15.
Figure 17:
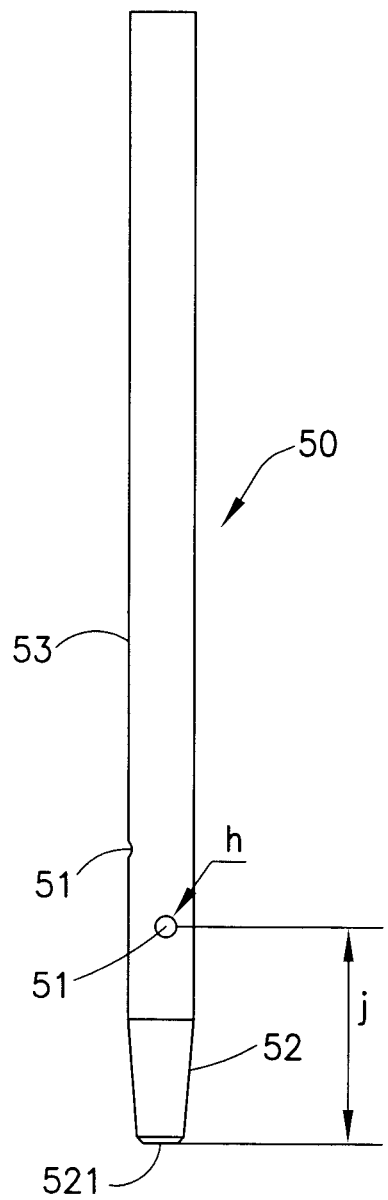
FIG. 17 is a right side view of the catheter of FIG. 16.
Figure 18:
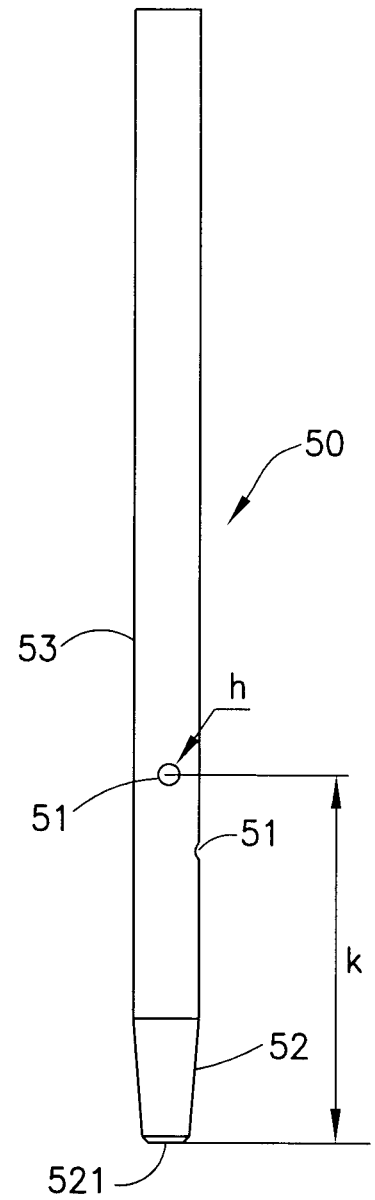
FIG. 18 is a left side view of the catheter of FIG. 16.

FIG. 15 illustrates another embodiment of the present invention, in which there are staggered single-side holes 51 that are placed along the length of the catheter tubing 53, although only one side-hole is illustrated in FIG. 15 due to the orientation of the perspective view. The locations of the holes 51 are more clearly illustrated in FIGS. 16 to 18. FIG. 16 is a front view of the catheter 50. FIG. 17 is a right side view of the catheter 40, and FIG. 18 is a left side view of the catheter 40. The staggering angle is not limited to the depicted 90°, and may include other angles, such as 45° or 180°. The outer diameter "g" of the catheter 50 is approximately 0.71 mm+0.04 mm. The diameter "h" of the side port 51 is approximately 0.20 mm.

The catheter 50 comprises a tubing 53, a tapered tip 52 at one end of the tubing 53 having an exit hole or tip hole 521, and an end portion 54 (simplified) opposite the tip 52. The staggered layout of the perforated holes 51 provides sufficient strength for the catheter 50 that the catheter 50 will not easily collapse during insertion. Further, this arrangement provides for sufficient catheter material to be formed around each of the three staggered holes 51. Each of the perforated holes 51 are shown as having different distances from the tip hole 521, such as "'"=3.0 mm, "j"=2.0 mm, and "k"=4.0 mm, as is illustrated in FIG. 16 to FIG. 18. The number of staggered perforated holes 51 or side ports can be two, three, or more.

Figure 19:
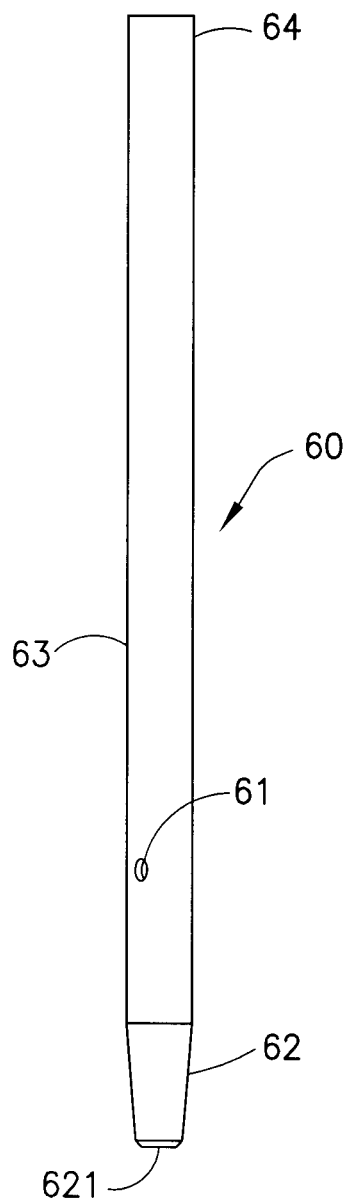
FIG. 19 is a perspective view of a catheter that is provided with a single through hole in accordance with an embodiment of the present invention.
Figure 20:
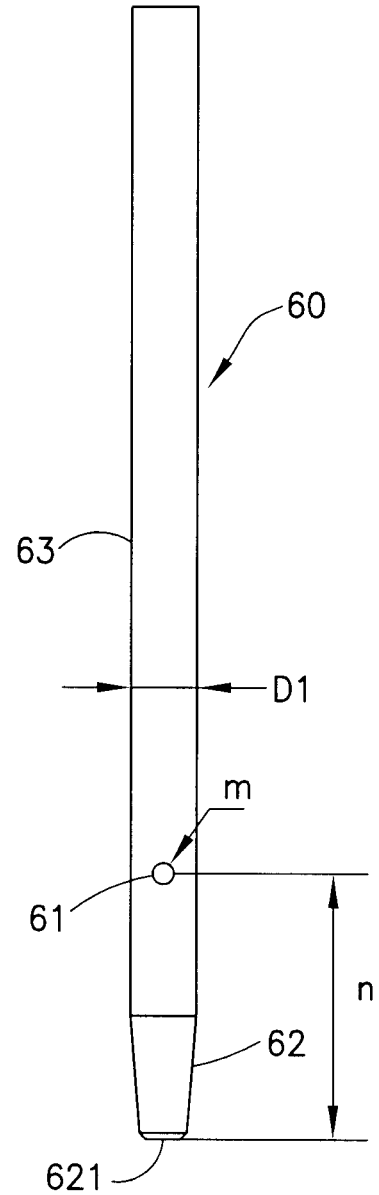
FIG. 20 is front view of the catheter of FIG. 19.
Figure 21:
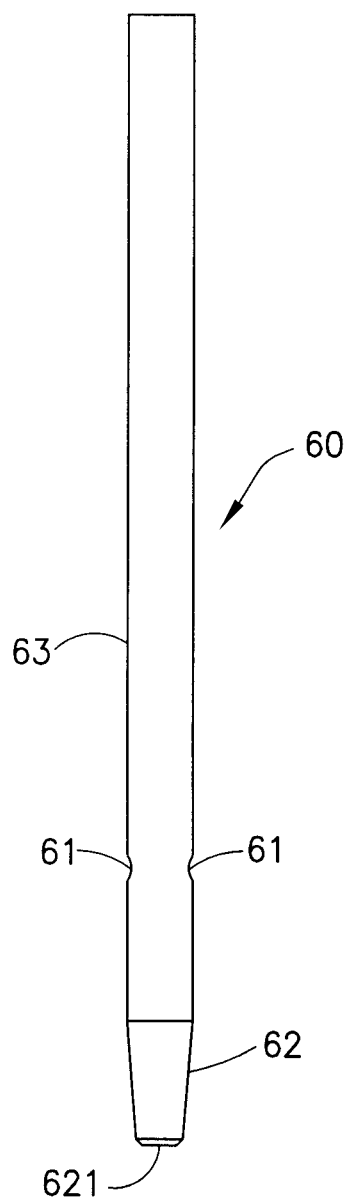
FIG. 21 is a side view of the catheter of FIG. 20.

FIG. 19 illustrates another embodiment, in which a catheter 60 includes a single through-hole 61 that extends from one sidewall of the tubing 63 through an opposite side thereof, as is more clearly illustrated in FIGS. 20 and 21. The catheter 60 includes a tubing 63, a tapered tip 62 at one end of the tubing 63, a tip hole 621, and an end portion 64 (simplified) at an opposite end of the tip 62. The two holes 61 formed by the single through-hole have the same distance from the tip hole 621, as is illustrated in FIG. 20. Such arrangement provides for sufficient strength of the catheter 60 to withstand the impact forces during catheter insertion. The outer diameter "D1" of the catheter 60 is approximately 0.71 mm. The diameter "m" of the holes 61 is approximately 0.25 mm. The distance "n" from the tip hole 621 to the holes 61 is approximately 3.0 mm.

Figure 22:
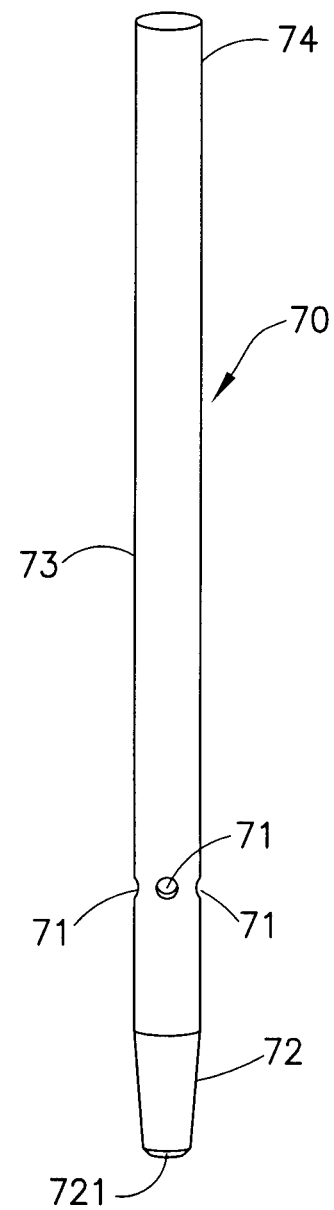
FIG. 22 is a perspective view of a catheter that is provided with a two through holes on the same plane in accordance with an embodiment of the present invention.
Figure 23:
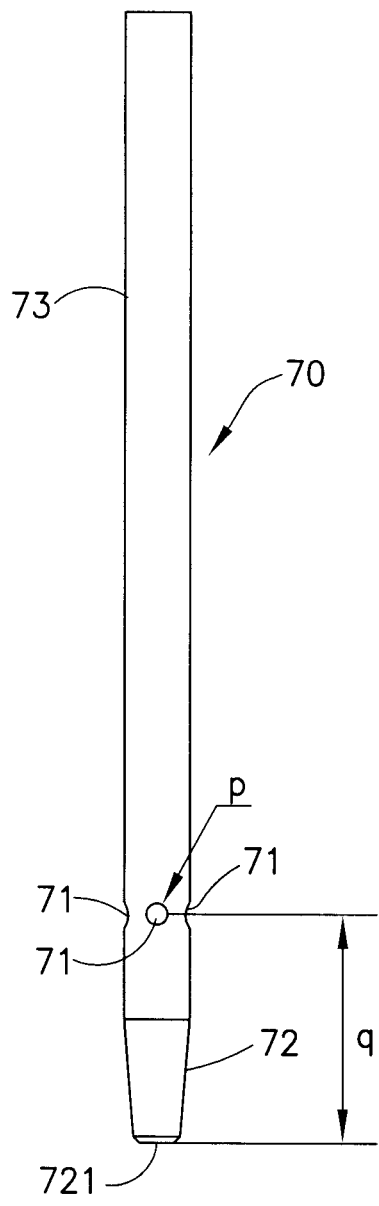
FIG. 23 is front view of the catheter of FIG. 22.
Figure 24:
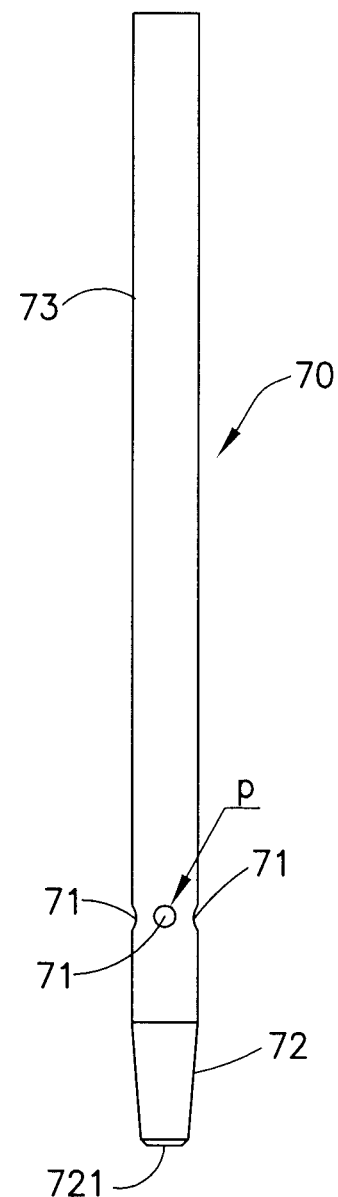
FIG. 24 is a side view of the catheter of FIG. 23.

FIG. 22 illustrates another embodiment in which there are two through-holes that form four side holes 71 equally distanced from the tip hole 721, as illustrated in FIGS. 23 and 24. The diameter "p" of the side holes 71 is approximately 0.25 mm. The catheter 70 includes a tubing 73 with a tapered tip 72 on one end with a tip hole 721, and an end portion 74 (simplified). It is noted that due to the presence of the four side port holes 71 along the same plane, such a catheter design may be more susceptible to collapsing at the plane of the perforations during insertion of the catheter 70. This is generally due to the reduced amount of material between the holes 71, resulting in a design that may be structurally weak. But such a layout in which the perforated holes are at or close to the tip 72 is desirable to reduce the risk of infusate leakage if the desired infusion site is proximate to the tip hole 721. The distance "q" between the side holes 71 and the tip hole 721 is approximately 2.03 mm. Structural integrity can be maintained by using stronger or thicker material for the catheter.

Figure 25:
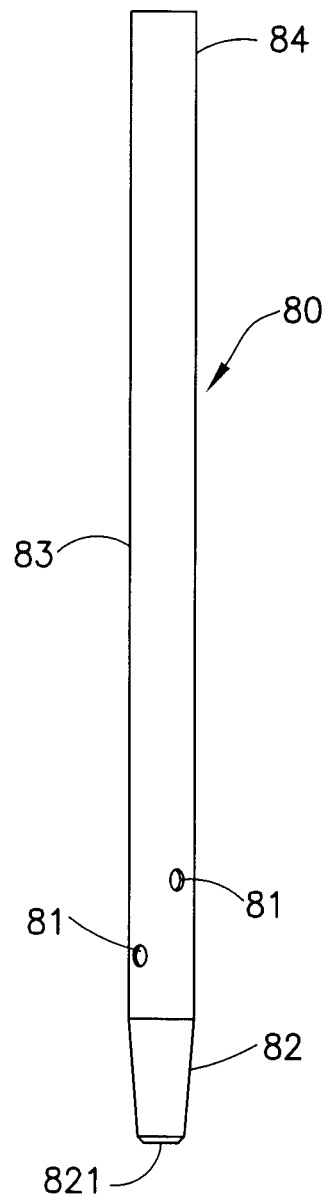
FIG. 25 is a perspective view of a catheter that is provided with two through holes on different planes in accordance with an embodiment of the present invention.
Figure 26:
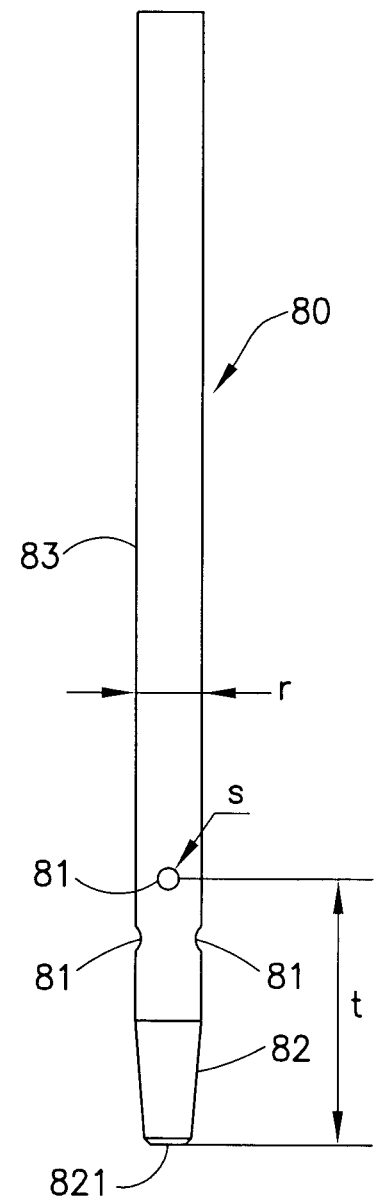
FIG. 26 is front view of the catheter of FIG. 25.
Figure 27:
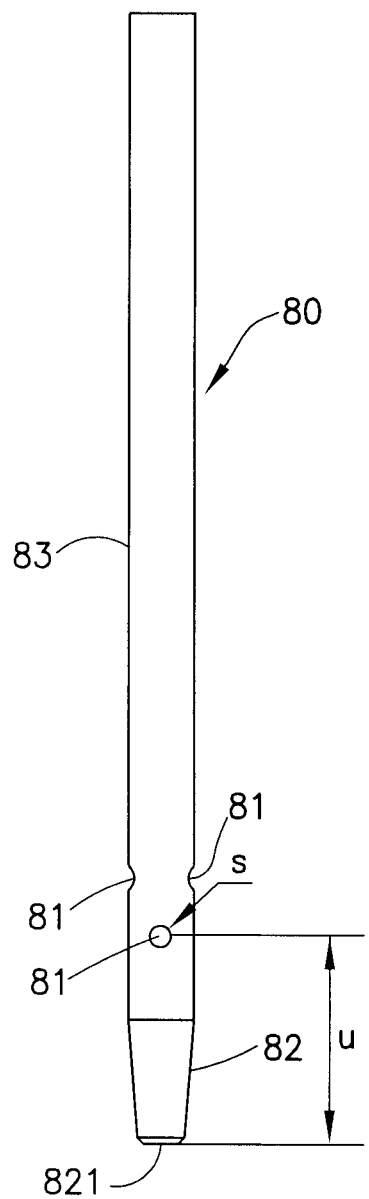
FIG. 27 is a side view of the catheter of FIG. 26.

FIG. 25 illustrates an embodiment of the present invention in which there are two staggered through-holes that form four side holes or ports 81. FIG. 26 is a front view of the catheter 80 and FIG. 27 is a side view of the catheter 80.

In this embodiment, a first set of two of the through-holes or side ports 81 are located at the same plane and a second set of two other side ports 81 are located at a different plane. In other words, a through hole forms two side ports. The diameter "s" of the side ports 81 is approximately 0.15 mm. The holes are located so that the first set of the through-holes are distanced equally from the tip hole 821 (distance "t"=3.0 mm), and the second set of through-holes 81 are spaced equally from the tip hole 821 (distance u=2.0 mm), as illustrated in FIGS. 26 and 27. The outer diameter "r" of the catheter 90 is approximately 0.71 mm+0.04 mm. Such an arrangement provides for sufficient catheter material to be formed around each of the holes 81 to maintain structural integrity of the catheter 80 during use. The catheter 80 includes a tubing 83, a tip 82 at one end of the tubing 83, with a tip hole 821, and an end portion 84 (simplified) opposite the tip 82.

Figure 28:
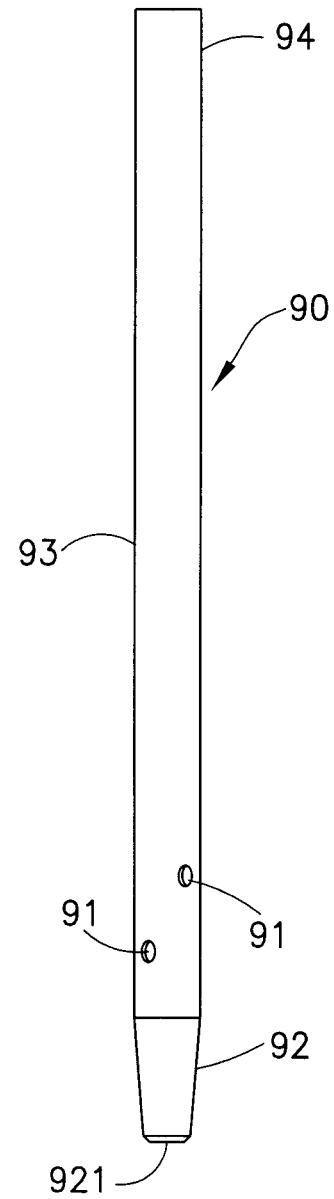
FIG. 28 is a perspective view of a catheter that is provided with two through holes of a larger diameter on different planes in accordance with an embodiment of the present invention.
Figure 29:
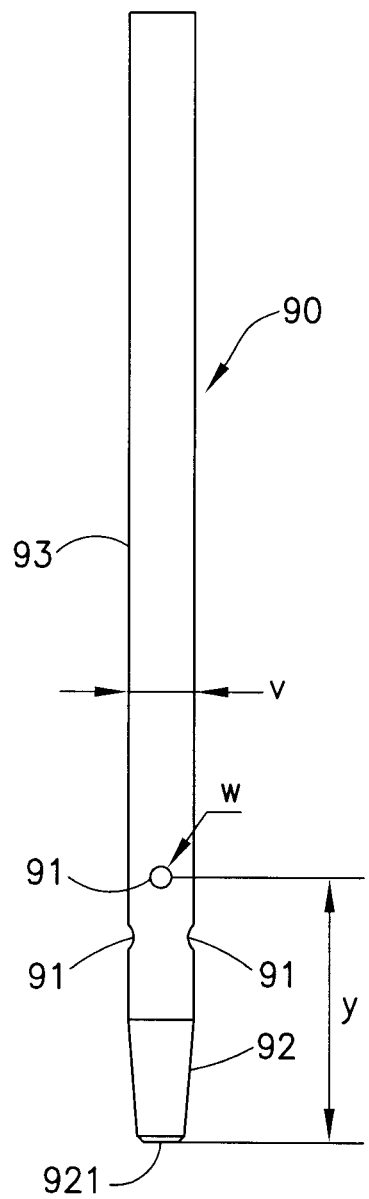
FIG. 29 is front view of the catheter of FIG. 28.
Figure 30:
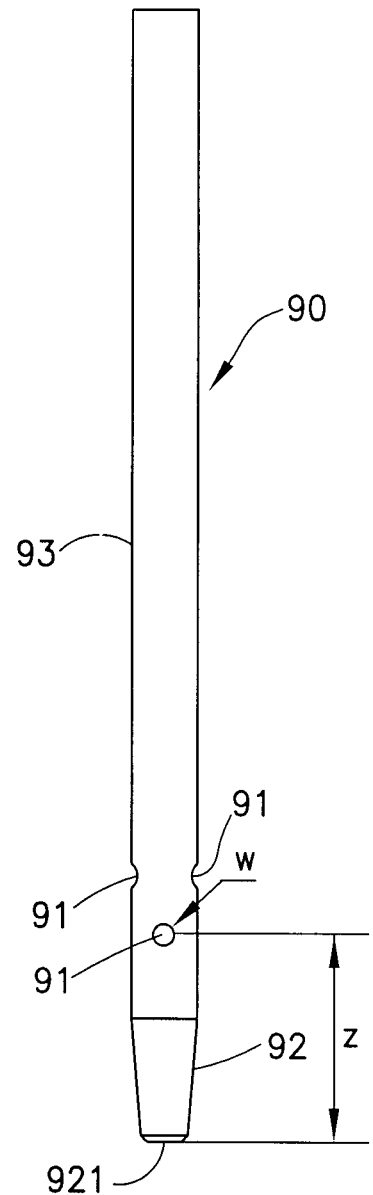
FIG. 30 is a side view of the catheter of FIG. 28.

FIG. 28 illustrates another embodiment of the present invention in which two staggered through-holes are formed on the catheter 90, in order to form four side holes 91. The through-holes are formed on different circumferential orientations. The embodiment of FIG. 28 is similar to the embodiment of FIGS. 25-27, differing only in the diameter of the side holes. FIG. 29 is a front view of the catheter 90 and FIG. 30 is a side view of the catheter 90. In this embodiment, the outer diameter "v" of the catheter 90 is approximately 0.71±0.04 mm. The diameter of the side port "w" is approximately 0.25 mm. The distances "y" and "z" from the sets of side ports 91 are approximately 3.0 mm and 2.0 mm, respectively.

In general, the size of the side ports and the location thereof on the catheter can be varied. The locations of the side ports correspond to a catheter for which the tip is generally deployed to a depth of about 6.0 mm from the skin's surface. The side ports can be on the tubing or at the tip, near the tip hole, or at a junction between the tip and the tubing, or at any other location on the catheter. As the introducer needle of an infusion set penetrates the skin, the skin initially resists penetration and deforms in the shape of an inverted tent (known commonly in the art as "tenting"). The size of the side holes or ports and their locations relative to the catheter tip are factors that should be taken into account to reduce insertion problems, such as excessive tenting, as well as leakage from the infusion site. Because the introducer needle is inserted through the catheter for the purpose of inserting the catheter into the skin, the dimensions and configurations of the catheter can affect the amount of tenting. Generally a catheter with thin walls may cause less tenting than a catheter with thicker walls. Excessive tenting may result in improper insertion of the catheter at the desired depth of the skin. Leakage at the infusion site may occur if the catheter is not properly inserted to the targeted tissue layer of the skin, and excessive tenting can cause such leakage.

Figure 31:
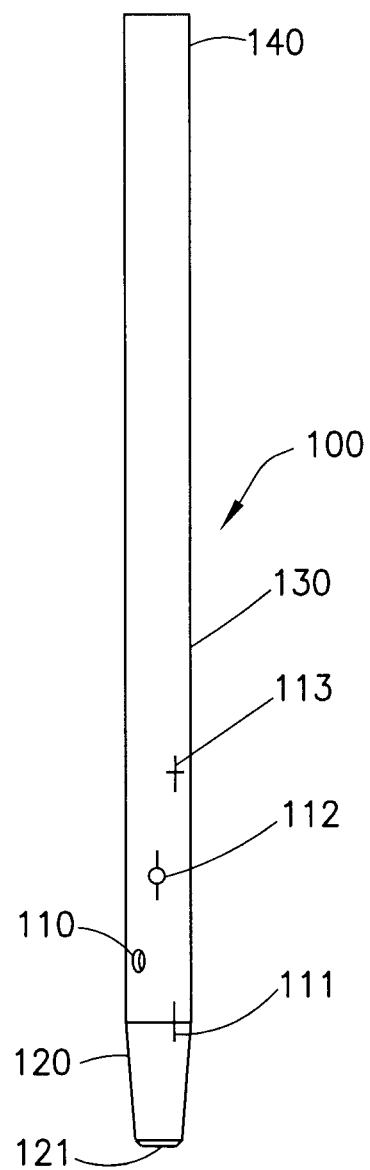
FIG. 31 is a perspective view of a catheter that is provided with a combination of one or more side ports and splits in accordance with an eighth embodiment of the present invention.

FIG. 31 illustrates another embodiment of the present invention in which the catheter 100 includes a side port 110, a single split 111, a cross split 113 and a split hole 112 (in which a hole is formed on a split). This embodiment illustrates that the various openings, including side holes and splits may be used in combination to form secondary or additional pathways in a catheter. As with other embodiments, the catheter 110 includes a tubing 130, a tapered tip 120 having a tip hole 121, and an end portion 140 (simplified) opposite the tip 120.

A preferred embodiment of a side ported catheter for delivery into subcutaneous tissue has a deployment depth of about 6 mm, with catheter port(s) within 2 mm of the catheter tip (opening), and ideally within 1 mm of the catheter tip. Such a catheter is preferably between 24G and 28G and made of polyurethane, polyolefin or fluorinated polymer such as polytetrafluoroethylene (PTFE) or fluorinated ethylene propylene (FEP). The catheters can also be made of silicone and various additives can be incorporated to improve mechanical strength and other properties. FEP is generally preferred over PTFE due to its thermoplastic properties that improve the effectiveness of the catheter forming process. It is preferred that the side ports on the catheter are formed by lasing or mechanical drilling, processes that are familiar to those skilled in the art. The formation of the side ports can also be incorporated into the catheter molding process.

Preclinical studies were conducted to determine the effectiveness of side ported catheters. From the preclinical studies, it was discovered that adding side ports to catheters significantly reduced the rate of occlusion alarms with generic ambulatory insulin infusion pumps that are commercially available. The side ported 6 mm catheters were tested along with un-ported, conventional 6 mm catheters. The conventional 6 mm catheters experienced occlusions alarms in 4 out of 16 pump devices tested on swine. In contrast, side ported 6 mm catheters experienced pump occlusion alarms in 0 of 48 pump devices, when tested under the same conditions.

In the preclinical studies mentioned above, side ported catheters of three different configurations were tested (see FIGS. 32-34). The side port catheter illustrated in FIG. 32 includes two ports that are on different planes, with the ports being staggered by 180 degrees and being 1.0 mm and 1.5 mm from the tip ($x_1$=1.0 mm; $x_2$=1.5 mm). The side ported catheter illustrated in FIG. 33 includes a through-hole on the same plane that forms two side ports ($x_1$=1.0 mm from the tip). The side ported catheter illustrated in FIG. 34 includes a single side port ($x_1$=1.0 mm from the tip). The configurations above are similar to those that are illustrated in FIGS. 12-21, except that the side ports are located on the tapered distal portions of the catheter and closer to the tip opening.

Figure 35:
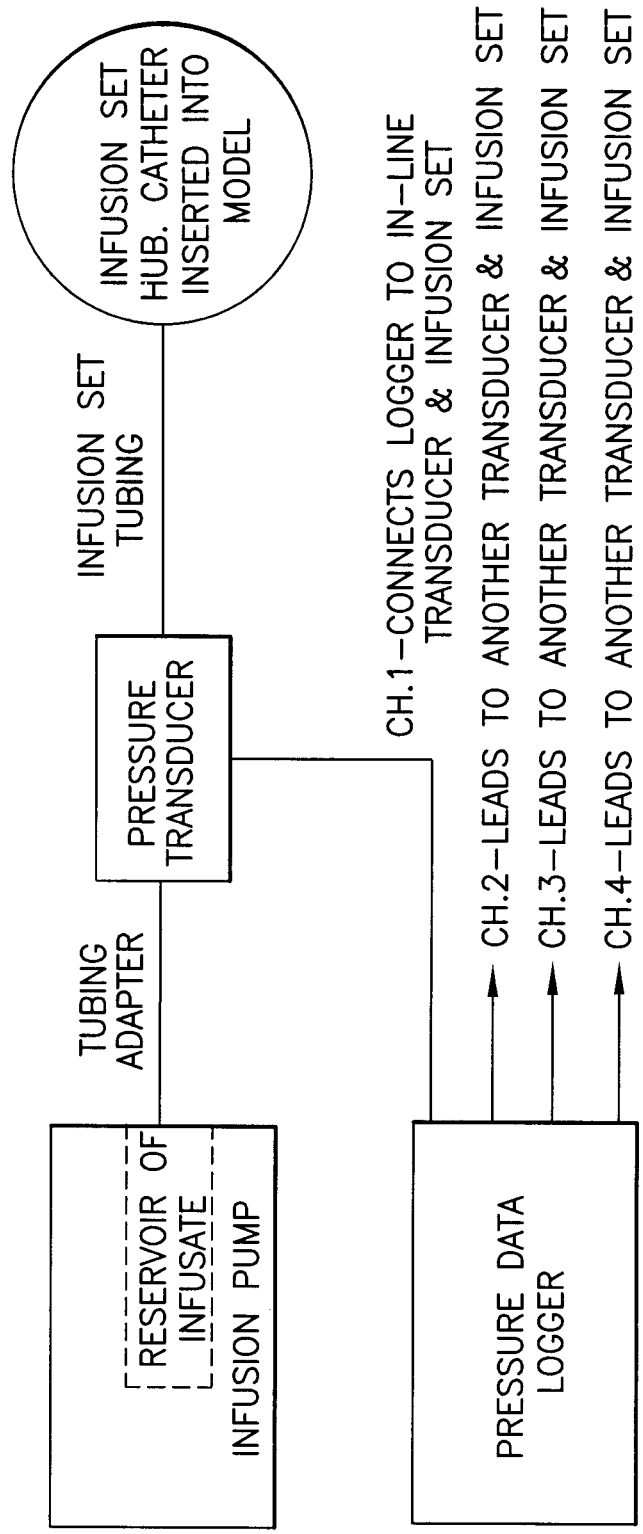
FIG. 35 is a schematic diagram of a pressure system and infusion device configuration in accordance with an embodiment of the present invention that was used in preclinical studies.

FIG. 35 is a schematic diagram of an in-line infusion pressure data collection system and its configuration with infusion sets that was used in preclinical testing. FIG. 35 shows a pressure data logger interfaced with a pressure transducer that is placed in-line via Luer connectors with the infusion set and an adapter to the reservoir containing the infusate. As the infusion pump operates, the pressure data logger stores the in-line infusion pressure profile. Rising infusion pressure indicates a flow restriction or occlusion.

In one preclinical study, swine were placed under anesthesia and 64 infusion sets (n=16 each of standard, non-ported conventional 24G, 6.0 mm infusion catheters and n=16 each of 3 configurations of side ported catheters illustrated in FIGS. 32, 33 and 34) were inserted in a 4×4 grid pattern. All infusion sets were connected to in-line infusion pressure data loggers described in FIG. 35. A specific infusion profile of bolus (high infusate delivery over a short period of time) and basal (low infusate delivery over extended periods of time) infusion was delivered over the course of this study. Flow interruptions as interpreted from the infusion pressure profiles were significantly decreased in each side-ported catheter configuration relative to the standard catheter configuration.

There was an 83% reduction in the number of flow interruptions and a 97% reduction in percent of total infusion time with flow interrupted for infusion sets with the side-ported catheters as compared with infusion sets with standard (non-ported) catheters. Visual inspection of the pressure profile plots also led to the following observations: peak bolus pressures were lower for ported catheters than non-ported ones; overall basal infusion pressures were lower for ported catheters than non-ported ones; and the insertion effect (flow interruption upon insertion as indicated by a rise in infusion pressure) during the first 4 hour basal infusion period was reduced or eliminated in all of the side-ported catheter configurations relative to the non-ported catheters.

The preclinical studies above confirmed that standard catheters with single openings at their tip (without any side-port(s)) experience frequent flow interruptions that result in non-delivery of insulin over durations that range from minutes to hours. In a swine study conducted using infusion catheters over a nine hour period, the mean percent time that flow was interrupted for control catheters (unported) was 34.5 percent. In contrast, the mean percent time that flow was interrupted in ported catheters was less than one (1.0) percent in all configurations tested. The preclinical studies above confirmed the improvements of the side-ported catheters over the standard non-ported catheters.

Further preclinical studies on swine confirmed that the distance of the side-port(s) from the catheter tip hole affected the deposition of the infusate. A fluoroscopy study in a swine model was conducted to determine the boundary conditions of side-port locations for successful subcutaneous infusion through evaluation of single side-ported catheters with side-ports placed over a range of distances (0.5-4.0 mm) from the catheter tip hole, as illustrated in FIG. 36. The single side-ported catheters were numbered 1 to 4. In the preclinical studies, catheters that protrude into the skin with a 6.0 mm length and side-port(s) at 0.5 mm or 1.0 mm from the catheter tip hole resulted in infusate depot locations that were indistinguishable from un-ported catheters and did not result in infusate leakage. Catheters with side-ports at 2.0 mm from the catheter tip had shallower deposition, but also delivered subcutaneously without leakage. However, catheters with ports at 4.0 mm from the catheter tip experienced significant leakage between the catheter and the skin surface.

In the study of the single side-ported catheters, a typical one being illustrated in FIG. 36, the catheters were each connected to a reservoir filled with Iohexol in a generic ambulatory insulin infusion pump. Each infusion device with a side-ported catheter was inserted using manual insertion into the flank of an anesthetized swine. Once the infusion device was inserted, a 10U bolus of Iohexol was delivered while viewing the infusion site under a fluoroscope. It was observed that the frequency of leakage between the catheter and skin increases as the side-port distance (x) increases from the catheter tip hole. A catheter (port 4 mm) having a side-port 4 mm from the tip hole had 6 of the 7 leakages observed in the study. Port 2 mm and Port 3 mm devices resulted in significantly shallower depots than the control, Port 0.5 mm, and Port 1 mm devices. The study indicated that port placement (x) within 1.0 mm from the catheter tip hole or less on a 6.0 mm catheter results in infusate deposition that is similar to catheters with only a single hole in the catheter tip.

Additional preclinical studies indicated that the catheter material and wall thickness may affect the performance of catheters in general and particularly affects the performance of catheters with side port(s). Thinner catheter tip designs can result in catheter tip deformation that leads to permanent occlusion of the catheter. A minimum wall thickness for a side-ported catheter is preferred to maintain catheter tip patency. Preclinical studies were performed on single side-ported 24G and 28G catheters. For a 24G catheter, a minimum wall thickness at the tip of 0.003 inch (0.076 mm) is preferred for PTFE and FEP catheter materials. The catheter material can include silicone or other suitable material. A catheter wall thickness at the tip of 0.002 inch (0.051 mm) resulted in catheter deformation and occlusion in 24G, 26G, and 28G experimental and commercial devices.

Catheters having a secondary fluid pathway, such as a side port, may be less likely to bend or kink when attached to a patient. In addition, deformations at the catheter tip appear to be less than with ordinary catheters, upon use. Moreover, an advantage of a split catheter (i.e., one having one or more splits on the sidewall of the catheter) is that because the splits are generally flush with the surface of the sidewall, the split catheter is less likely to snag on the patient's skin during insertion.

The configuration of a catheter having a plurality of side openings or splits or a combination thereof may be used in catheters that are inserted into the user's skin at an angle (e.g. 30 degrees), as opposed to a vertical insertion. An advantage to this configuration is that the skin can more readily absorb infusate due to the additional number of side openings or slits along an elongated length.

Although only a limited number of exemplary embodiments of the present invention have been described in detail above, those skilled in the art will readily appreciate that many modifications are possible in the exemplary embodiments without materially departing from the novel teachings and advantages of this invention. Accordingly, all such modifications are intended to be included within the scope of this invention as defined in the appended claims and their equivalents.

The invention claimed is:

1. A catheter comprising:
a flexible elongate member comprising a sidewall having a wall thickness of not more than 0.004 inches, the sidewall forming a single lumen between a first end and a second end, and an opening at each of the first end and the second end, a proximal one of said openings connected to a wedge; the elongate member having a length between said first and second ends for insertion of the second end into a dermal layer of a patient;
wherein the first end of the elongate member is in fluid communication with an infusion pump that pumps fluid through the catheter at a predetermined flow rate and at a pressure below a cracking pressure when the second end of the elongate member is not occluded;
a primary fluid pathway through the elongate member between the opening at the first end and the opening at the second end of the elongate member; the primary fluid pathway having a proximal end in fluid communication with a fluid reservoir and permitting fluid to flow through the primary fluid pathway and to exit the second end while the pressure is below the cracking pressure; and
a secondary fluid pathway in fluid communication with the primary fluid pathway;
wherein the secondary fluid pathway comprises one or more side flaps in the sidewall of the elongate member, the one or more side flaps configured to release, depending on their number, size and location on the elongate member, controlled amounts of fluid into the skin of a patient, the secondary fluid pathway permitting increased flow of fluid through the secondary fluid pathway into the dermal layer of the patient by increasing in size if the primary fluid pathway is occluded at the second end of the elongate member such that pressure of the fluid exceeds the cracking pressure;
wherein the one or more side flaps are formed by two line segments joined at one end of each line segment, the two line segments having bilateral symmetry with respect to a primary axis of the catheter;
wherein the one or more side flaps remain closed while fluid pressure in the primary fluid pathway is below the cracking pressure, and open when the fluid pressure in the primary fluid pathway exceeds the cracking pressure; and
wherein the one or more side flaps have a circumferential length of 60-120 degrees of a circumference of the catheter.

2. The catheter as claimed in claim 1, wherein fluid introduced into the opening at the first end flows out of the catheter via one or both of the opening at the second end and the secondary fluid pathway.

3. The catheter as claimed in claim 1, wherein the one or more flaps are positioned at the second end.

4. The catheter as claimed in claim 3, wherein the one or more flaps is or are positioned on the sidewall, between the openings of the first and second ends.

5. The catheter as claimed in claim 3, wherein the one or more flaps are staggered along a length of the sidewall.

6. The catheter as claimed in claim 1, wherein the catheter is configured to be used with an infusion set.

7. The catheter as claimed in claim 1, wherein the catheter comprises plastic material.

8. The catheter of claim 1, wherein the secondary fluid pathway is normally closed, and opens when fluid within the catheter exceeds the cracking pressure, and closes when the fluid within the catheter decreases below the cracking pressure.

9. A catheter comprising:
an elongate member comprising a sidewall having a thickness not more than 0.004 inches, a first end and a second end, and an opening at each of the first end and the second end, a proximal one of said openings connected to a wedge; the elongate member having a length between said first and second ends for insertion of the second end into a dermal layer of a patient;
a primary fluid pathway through the elongate member between the opening at the first end and the opening at the second end of the elongate member; the primary fluid pathway having a proximal end in fluid communication with an infusion pump that pumps fluid through the catheter and out the second end at a predetermined flow rate and while below a cracking pressure when the second end is not occluded; and
a secondary fluid pathway in fluid communication with the primary fluid pathway;
wherein the secondary fluid pathway comprises a self-closing opening in the sidewall of the elongate member; the secondary fluid pathway permitting fluid flow by increasing in size if the primary fluid pathway is occluded at the second end of the elongate member such that pressure of the fluid exceeds the cracking pressure;
wherein the self-closing opening is configured as a flap formed by two line segments joined at one end of each line segment, the two line segments having bilateral symmetry with respect to a primary axis of the catheter;
wherein the flap has a circumferential length of 60-120 degrees of a circumference of the catheter; and
wherein the self-closing opening remains closed while fluid pressure in the primary fluid pathway is below the cracking pressure, and opens when the fluid pressure in the primary fluid pathway exceeds the cracking pressure.

10. The catheter as claimed in claim 9, wherein if fluid exceeds the cracking pressure, the self-closing opening opens to permit the fluid to flow out of the secondary fluid pathway, and when the pressure of the fluid in the primary fluid pathway decreases below the cracking pressure, the self-closing opening closes.

11. The catheter as claimed in claim 9, wherein fluid introduced into the opening at the first end flows out of the catheter via one or both of the opening at the second end and the secondary fluid pathway.

12. The catheter as claimed in claim 9, wherein the secondary fluid pathway comprises a plurality of slits.

13. The catheter as claimed in claim 9, wherein the secondary fluid pathway further comprises a side port.

14. The catheter as claimed in claim 13, wherein the side port is positioned at the second end.

15. The catheter as claimed in claim 9, wherein the secondary fluid pathway further comprises a plurality of side ports.

16. The catheter as claimed in claim 15, wherein the side ports are positioned at the second end.

17. The catheter as claimed in claim 15, wherein the side ports are positioned on the sidewall, between the openings of the first and second ends.

18. The catheter as claimed in claim 15, wherein the side ports are staggered along a length of the sidewall.

19. The catheter as claimed in claim 9, wherein the catheter is configured to be used with an infusion set.

20. The catheter as claimed in claim 9, wherein the catheter is flexible.

21. The catheter as claimed in claim 20, wherein the catheter comprises plastic material.

22. A method of administering infusate via a catheter, comprising the steps of:
providing the catheter comprising a flexible elongate member comprising a sidewall having a thickness not more than 0.004 inches, the sidewall forming a single lumen between a first end and a second end, and an opening at each of the first end and the second end, a primary fluid pathway through the elongate member between the openings of the first end and the second end of the elongate member; the primary fluid pathway having a proximal end in fluid communication with an infusion pump or fluid reservoir, and a secondary fluid pathway in fluid communication with the primary fluid pathway,
permitting fluid to flow through the primary fluid pathway and out the second end while a fluid pressure is below a cracking pressure;

wherein the secondary fluid pathway comprises one or more flaps in the sidewall of the elongate member, the flaps configured to release controlled amounts of infusate, depending on their number, size and location on the elongate member, into the skin of a patient;

inserting the catheter into a dermal layer of a patient; and administering infusate to the patient from the infusion pump or fluid reservoir at a predetermined flow rate and below the cracking pressure when the second end is not occluded via the primary fluid pathway of the catheter while a fluid pressure within the primary fluid pathway is below the cracking pressure and the one or more flaps remain closed; and continuing to administer infusate to the patient via the secondary fluid pathway if fluid pressure within the primary fluid pathway exceeds the cracking pressure by opening the one or more flaps and increasing a size of at least one of the one or more flaps;

wherein the one or more flaps are formed by two line segments joined at one end of each line segment, the two line segments having bilateral symmetry with respect to a primary axis of the catheter; and wherein the one or more flaps have a circumferential length of 60-120 degrees of a circumference of the catheter.

23. A method of administering infusate via a catheter, comprising the steps of:

providing the catheter comprising a flexible elongate member comprising a sidewall having a thickness of not more than 0.004 inches, a first end and a second end, and an opening at each of the first end and the second end, a proximal one of said openings connected to a wedge, a primary fluid pathway through the elongate member between the opening at the first end and the opening at the second end of the elongate member; the primary fluid pathway having a proximal end in fluid communication with an infusion pump that pumps fluid through the catheter at a predetermined flow rate and below a cracking pressure when the second end is not occluded, and a secondary fluid pathway in fluid communication with the primary fluid pathway, wherein the secondary fluid pathway comprises a self-closing opening in the sidewall of the elongate member;

inserting the catheter into dermal layer of a patient; and administering infusate to the patient through the primary fluid pathway and out the second end of the catheter while fluid pressure within the primary fluid pathway is below the cracking pressure and the self-closing opening is closed; and continuing to administer infusate to the patient via the secondary fluid pathway if fluid pressure within the primary fluid pathway exceeds the cracking pressure by opening the self-closing opening and increasing a size of the self-closing opening;

wherein the self-closing opening is configured as a flap formed by two line segments joined at one end of each line segment, the two line segments having bilateral symmetry with respect to a primary axis of the catheter; and wherein the flap has a circumferential length of 60-120 degrees of a circumference of the catheter.

24. A method of administering infusate via a catheter, comprising the steps of:

providing the catheter comprising a primary fluid pathway through a flexible elongate member; the primary fluid pathway having a proximal end in fluid communication with an infusion pump that pumps fluid through the catheter at a predetermined flow rate and below a cracking pressure when a distal end of the elongate member is not occluded, the elongate member connected at the proximal end to a wedge, a secondary fluid pathway in fluid communication with the primary fluid pathway, the secondary fluid pathway comprising a self-closing opening at a sidewall of the elongate member;

inserting the catheter into a dermal layer of a patient; and administering infusate to the patient through the primary fluid pathway and out the distal end of the elongate member while fluid pressure within the primary fluid pathway is below a cracking pressure and the self-closing opening is closed; and continuing to administer infusate to the patient via the secondary fluid pathway if fluid pressure within the primary fluid pathway exceeds the cracking pressure by opening the self-closing opening and increasing a size of the self-closing opening;

wherein the self-closing opening is configured as a flap formed by two line segments joined at one end of each line segment, the two line segments having bilateral symmetry with respect to a primary axis of the catheter;

wherein the catheter has a sidewall having a thickness of not more than 0.004 inches; and wherein the one or more flaps have a circumferential length of 60-120 degrees of a circumference of the catheter.

* * * * *